United States Patent
Speelmans et al.

(10) Patent No.: US 10,426,791 B2
(45) Date of Patent: *Oct. 1, 2019

(54) SYNERGISM OF GOS AND POLYFRUCTOSE

(71) Applicant: N.V. Nutricia, Zoetermeer (NL)

(72) Inventors: Gelske Speelmans, Utrecht (NL); Maria Johanna Adriana Petronella Govers, Utrecht (NL); Jan Knol, Utrecht (NL); Eric Alexander Franciscus Van Tol, Arnhem (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,746

(22) Filed: Jul. 11, 2017

(65) Prior Publication Data

US 2018/0153923 A1 Jun. 7, 2018

Related U.S. Application Data

(63) Continuation of application No. 13/750,749, filed on Jan. 25, 2013, now abandoned, which is a continuation of application No. 11/569,239, filed as application No. PCT/NL2005/000372 on May 17, 2005, now abandoned.

(30) Foreign Application Priority Data

May 17, 2004 (EP) ..................... 04076479

(51) Int. Cl.
| | | |
|---|---|---|
| A61K 31/733 | (2006.01) | |
| A23L 5/00 | (2016.01) | |
| A23L 33/125 | (2016.01) | |
| A61K 31/702 | (2006.01) | |
| A61K 31/715 | (2006.01) | |
| A23L 29/30 | (2016.01) | |
| A23L 33/00 | (2016.01) | |
| A61K 31/01 | (2006.01) | |
| A23L 29/244 | (2016.01) | |
| A23L 33/10 | (2016.01) | |
| A23L 33/22 | (2016.01) | |
| A23L 7/00 | (2016.01) | |

(52) U.S. Cl.
CPC ............ *A61K 31/733* (2013.01); *A23L 5/00* (2016.08); *A23L 29/244* (2016.08); *A23L 29/30* (2016.08); *A23L 33/10* (2016.08); *A23L 33/125* (2016.08); *A23L 33/22* (2016.08); *A23L 33/40* (2016.08); *A61K 31/01* (2013.01); *A61K 31/702* (2013.01); *A61K 31/715* (2013.01); *A23L 7/00* (2016.08); *A23V 2002/00* (2013.01); *A23V 2200/318* (2013.01)

(58) Field of Classification Search
None
See application file for complete search history.

(56) References Cited

U.S. PATENT DOCUMENTS

| | | |
|---|---|---|
| 2,981,629 A | 4/1961 | Ginnette et al. |
| 3,956,228 A | 5/1976 | Nogami et al. |
| 4,237,118 A | 12/1980 | Howard |
| 4,412,946 A | 11/1983 | Zalisz et al. |
| 4,438,147 A | 3/1984 | Hedrick, Jr. |
| 5,292,723 A | 3/1994 | Audry et al. |
| 5,374,657 A | 12/1994 | Kyle |
| 5,444,054 A | 8/1995 | Garleb et al. |
| 5,472,952 A | 12/1995 | Smidt et al. |
| 5,502,041 A | 3/1996 | Moen et al. |
| 5,531,988 A | 7/1996 | Paul |
| 5,612,320 A | 3/1997 | Wurtman et al. |
| 5,629,023 A | 5/1997 | Bland |
| 5,629,040 A | 5/1997 | Takemori et al. |
| 5,709,888 A | 1/1998 | Gil et al. |
| 5,733,579 A | 3/1998 | Wolf et al. |
| 5,744,134 A | 4/1998 | Paul |
| 5,773,094 A | 6/1998 | Kruckel |
| 5,776,887 A | 7/1998 | Wibert et al. |
| 5,792,754 A | 8/1998 | Green et al. |
| 5,827,526 A | 10/1998 | Dohnalek et al. |
| 5,840,361 A | 11/1998 | Theuer et al. |
| 5,846,569 A | 12/1998 | Anderson et al. |
| 5,882,648 A | 3/1999 | Yoshihara et al. |
| 6,051,260 A | 4/2000 | Liska et al. |
| 6,197,758 B1 | 3/2001 | Ohtsuki et al. |
| 6,231,889 B1 | 5/2001 | Richardson et al. |
| 6,306,908 B1 | 10/2001 | Carlson et al. |
| 6,337,137 B1 | 1/2002 | Koldijk et al. |
| 6,426,110 B1 | 7/2002 | Basa |
| 6,451,584 B2 | 9/2002 | Tomita et al. |

(Continued)

FOREIGN PATENT DOCUMENTS

| | | |
|---|---|---|
| AU | 199728718 B2 | 7/1997 |
| CA | 2340103 | 2/2000 |

(Continued)

OTHER PUBLICATIONS 14.0 Spray Drying, obtained from http://class.fst.ohio-state.edu/Dairy_Tech/14Spraydrying.htm, Mar. 1, 2000, 15 pages.
Agostoni et al., "From nutrient composition to infants' function," Minerva Pediatrica, vol. 47, No. 3, 1995, pp. 181-194.
AIDS Fact Sheet: T-cell tests; also available at http://web.archive.org/web/20040217112225/http://www.aids.org/factSheets/124-T-Cell-Tests.html, published 2004; last viewed Oct. 21, 2009.
Alanate 385 Dispersible Calcium Caseinate, specification sheet, 2 pages, no date available (cited in US 2006-0110516, Office Action dated Mar. 1, 2010).
Alles et al., "Current trends in the composition of infant milk formulas," Current Paediatrics, vol. 14, 2004, pp. 51-63.

(Continued)

*Primary Examiner* — Shaojia A Jiang
*Assistant Examiner* — Bahar Craigo
(74) *Attorney, Agent, or Firm* — Gilberto M. Villacorta; Sunit Talapatra; Foley & Lardner LLP

(57) ABSTRACT

The present invention relates to the field of prebiotics. Provided are uses for compositions comprising synergistically effective amounts of polyfructose and galactooligosaccharides (GOS).

13 Claims, 6 Drawing Sheets

(56) References Cited

U.S. PATENT DOCUMENTS

| | | |
|---|---|---|
| 6,468,987 B1 | 10/2002 | Demichele et al. |
| 6,576,251 B1 | 6/2003 | Stahl et al. |
| 6,632,445 B2 | 10/2003 | Richardson et al. |
| 6,645,543 B2 | 11/2003 | Gohman et al. |
| 6,713,113 B2 | 3/2004 | Bisperink et al. |
| 6,737,089 B2 | 5/2004 | Wadsworth et al. |
| 6,794,495 B1 | 9/2004 | Sorensen |
| 6,846,501 B2 | 1/2005 | Prosise et al. |
| 6,872,416 B2 | 3/2005 | Chmiel et al. |
| 6,974,841 B1 | 12/2005 | Rapisarda |
| 7,351,715 B2 | 4/2008 | Richardson et al. |
| 7,576,070 B2 | 8/2009 | Kunz et al. |
| 7,601,364 B2 | 10/2009 | Sawatzki et al. |
| 2002/0015760 A1 | 2/2002 | Prosise et al. |
| 2002/0016289 A1 | 2/2002 | Conneely et al. |
| 2002/0018839 A1 | 2/2002 | Chmiel et al. |
| 2002/0044988 A1 | 4/2002 | Fuchs et al. |
| 2002/0127322 A1 | 9/2002 | Bisperink et al. |
| 2002/0197313 A1 | 12/2002 | Richardson et al. |
| 2003/0022863 A1 | 1/2003 | Stahl et al. |
| 2003/0165604 A1 | 9/2003 | Tsubaki et al. |
| 2004/0018996 A1 | 1/2004 | Richardson et al. |
| 2004/0072791 A1 | 4/2004 | Kunz et al. |
| 2004/0122105 A1 | 6/2004 | Bettle et al. |
| 2004/0219188 A1 | 11/2004 | Comer et al. |
| 2006/0067921 A1 | 3/2006 | Conway |
| 2006/0110516 A1 | 5/2006 | Holtus et al. |
| 2007/0036839 A1 | 2/2007 | Tuduri et al. |
| 2007/0098762 A1 | 5/2007 | Stahl et al. |
| 2007/0110758 A1 | 5/2007 | Campbell et al. |
| 2007/0166446 A1 | 7/2007 | Boursier |
| 2008/0015166 A1 | 1/2008 | Van Tol et al. |
| 2008/0064656 A1 | 3/2008 | Van Tol |
| 2008/0138435 A1 | 6/2008 | Van Den Berg et al. |
| 2008/0171720 A1 | 7/2008 | Garssen et al. |
| 2008/0207559 A1 | 8/2008 | Sawatzki et al. |
| 2009/0082249 A1 | 3/2009 | Garssen et al. |
| 2010/0016214 A1 | 1/2010 | Sawatzki et al. |
| 2010/0069320 A1 | 3/2010 | Speelmans |
| 2010/0167982 A1 | 7/2010 | Van Tol et al. |
| 2011/0077189 A1 | 3/2011 | Vriesema |
| 2011/0236500 A1 | 9/2011 | Van Den Berg et al. |

FOREIGN PATENT DOCUMENTS

| | | |
|---|---|---|
| DE | 10027050 A1 | 2/1957 |
| DE | 28 44 861 A1 | 4/1980 |
| DE | 37 34 962 C1 | 1/1989 |
| DE | 19940011 A1 | 3/2001 |
| DE | 10136260 A1 | 2/2003 |
| EP | 0 355 905 A1 | 2/1990 |
| EP | 0 378 824 B1 | 7/1990 |
| EP | 0 382 355 B1 | 8/1990 |
| EP | 0 484 266 A2 | 5/1992 |
| EP | 0 504 055 A1 | 9/1992 |
| EP | 0 511 761 A1 | 11/1992 |
| EP | 0 524 796 A1 | 1/1993 |
| EP | 0 307 523 B1 | 3/1993 |
| EP | 0 596 717 A1 | 5/1994 |
| EP | 0 615 752 A1 | 9/1994 |
| EP | 0 641 562 A1 | 3/1995 |
| EP | 0 692 252 A1 | 1/1996 |
| EP | 0 705 539 A2 | 4/1996 |
| EP | 0 711 503 A2 | 5/1996 |
| EP | 0 756 828 A1 | 2/1997 |
| EP | 0 593 774 B1 | 6/1997 |
| EP | 0 813 815 A1 | 12/1997 |
| EP | 0 745 330 B1 | 10/1998 |
| EP | 0 745 001 B1 | 11/1998 |
| EP | 0 756 828 B1 | 11/1998 |
| EP | 0 958 825 A1 | 11/1999 |
| EP | 1 074 181 A1 | 2/2001 |
| EP | 1 105 002 B1 | 6/2001 |
| EP | 0 631 731 B1 | 9/2001 |
| EP | 1 155 627 A1 | 11/2001 |
| EP | 1 228 694 A1 | 8/2002 |
| EP | 0 941 088 B1 | 3/2003 |
| EP | 1 321 527 | 6/2003 |
| EP | 1 321 527 A1 | 6/2003 |
| EP | 1 454 990 | 9/2004 |
| EP | 1 597 978 A1 | 11/2005 |
| EP | 1 454 990 B1 | 2/2006 |
| EP | 0 723 951 A1 | 11/2006 |
| EP | 1 721 611 A1 | 11/2006 |
| EP | 1 723 951 A1 | 11/2006 |
| EP | 1 672 987 B1 | 5/2007 |
| EP | 1 815 755 B1 | 8/2007 |
| FR | 2781673 A1 | 2/2000 |
| FR | 2866203 A1 | 8/2005 |
| GB | 1 305 071 | 1/1973 |
| JP | 53-042340 A | 11/1978 |
| JP | 02-286058 A | 11/1990 |
| JP | 08-033448 A | 2/1996 |
| JP | 08-151328 A | 6/1996 |
| JP | 09-065855 | 3/1997 |
| JP | 10-175867 | 6/1998 |
| JP | 2003-146887 A | 5/2003 |
| JP | 2006-115826 | 5/2006 |
| NL | 1018832 C2 | 3/2003 |
| WO | WO-92/22588 A1 | 12/1992 |
| WO | WO-95/26646 A1 | 10/1995 |
| WO | WO-96/13271 A1 | 5/1996 |
| WO | WO-97/02829 A2 | 1/1997 |
| WO | WO-97/34615 A1 | 9/1997 |
| WO | WO-98/04270 | 2/1998 |
| WO | WO-98/06276 A1 | 2/1998 |
| WO | WO-98/11910 A1 | 3/1998 |
| WO | WO-98/15196 A1 | 4/1998 |
| WO | WO-98/26787 A1 | 6/1998 |
| WO | WO-98/31241 A1 | 7/1998 |
| WO | WO-98/46764 A1 | 10/1998 |
| WO | WO-99/53777 A1 | 10/1999 |
| WO | WO-00/08948 A2 | 2/2000 |
| WO | WO-01/41581 A1 | 6/2001 |
| WO | WO-01/60378 A2 | 8/2001 |
| WO | WO-01/78530 A2 | 10/2001 |
| WO | WO-02/42484 A2 | 5/2002 |
| WO | WO-02/47612 | 6/2002 |
| WO | WO-02/47612 A2 | 6/2002 |
| WO | WO-02/060283 A2 | 8/2002 |
| WO | WO-02/076471 A1 | 10/2002 |
| WO | WO-03/093322 A2 | 11/2003 |
| WO | WO-03/102205 A1 | 12/2003 |
| WO | WO-2004/000042 A2 | 12/2003 |
| WO | WO-2004/000340 A2 | 12/2003 |
| WO | WO-2004/019699 A1 | 3/2004 |
| WO | WO-2004/026294 A1 | 4/2004 |
| WO | WO-2004/052121 A1 | 6/2004 |
| WO | WO-2004/112508 A1 | 12/2004 |
| WO | WO-2004/112509 A2 | 12/2004 |
| WO | WO-2004/113415 A1 | 12/2004 |
| WO | WO-2005/039319 A1 | 5/2005 |
| WO | WO-2005/039597 A2 | 5/2005 |
| WO | WO-2005/067955 A1 | 7/2005 |
| WO | WO-2005/110121 A1 | 11/2005 |
| WO | WO-2005/122790 A1 | 12/2005 |
| WO | WO-2006/007676 A1 | 1/2006 |
| WO | WO-2006/014519 A1 | 2/2006 |
| WO | WO-2006/112694 A2 | 10/2006 |
| WO | WO-2006/112716 A2 | 10/2006 |
| WO | WO-2006/112717 A2 | 10/2006 |
| WO | WO-2007/016132 A2 | 2/2007 |
| WO | WO-2007/115210 A2 | 10/2007 |
| WO | WO-2009/096772 A1 | 8/2009 |
| WO | WO-2009/096789 A1 | 8/2009 |

OTHER PUBLICATIONS

Alter et al., "Sequential deregulation of NK cell subset distribution and function starting in acute HIV-1 infection," Blood, vol. 106, No. 10, Nov. 15, 2005, pp. 3366-3369.

Analysis of RAFTIMIX 10; RAFTIMIX® ST and RAFTILOSE® P95, (1995).

(56) References Cited

OTHER PUBLICATIONS

Anonymous, "Larch Arabinogalactan," Alternative Medicine Review, vol. 5, No. 5, 2000, pp. 463-466.
Barcelo et al., "Mucin secretion is modulated by luminal factors in the isolated vascularly perfused rat colon," Gut, vol. 46, 2000, pp. 218-224.
Bedell, G. N. et al., J. Clin. Invest., Measurement of the Volume of Gas in the Gastrointestinal Tract. Values in Normal Subjects and Ambulatory Patients, Mar. 1956, vol. 35, No. 3, pp. 336-345.
Bernhart et al., "Lactulose in Modified Milk Products for Infant Nutrition," J. Dairy Sci., 1956, pp. 399-400.
Blaut, M. (2002) Relationship of prebiotics and food to intestinal microflora. European Journal of Nutrition, vol. 41, suppl. 1, pp. I/11-I16.
Boehm et al., "Prebiotics and Immune Responses," Journal of Pediatric Gastroenterology and Nutrition, vol. 39, Jun. 2004, pp. S772-S773.
Boehm et al., "Supplementation of a bovine milk formula with an oligosaccharide mixture increases counts of faecal bifidobacteria in preterm infants," Fetal & Neonatal, vol. 86, No. 3, May 2002, pp. F178-F181.
Boehm, "Prebiotic concept for infant nutrition," Acta Paediatrica Suppl., vol. 441, 2003, pp. 64-67.
Boersma et al., "Vitamin E, lipid fractions, and fatty acid composition of colostrum, transitional milk, and mature milk: an international comparative study," American Journal of Clinical Nutrition, Dep. of Obstetrics & Gynaecology, State Univ. Groningen, EZ Groningen 9713, Netherlands, vol. 3, No. 5, 1991, p. 1197-1204.
Bouhnik et al., "Administration of Transgalacto-Oligosaccharides Increases Fecal Bifiobacteria and Modifies Colonic Fermentation Metabolism in Healthy Humans," American Society for Nutritional Sciences, 1997 pp. 444-448.
Breitkreutz et al., "Improvement of immune functions in HIV infection by sulfur supplementation: Two randomized trials," Journal of Molecular Medicine (Berlin), vol. 78, No. 1, 2000, pp. 55-62.
Buckler, "Prebiotics in infant nutrition," Internet article online Jul. 8, 2001, pp. 1-5 (XP002292254), retrieved from the Internet: URL:http://ww.se-neonatal.es/se-neonatal/oviedo2001/prebiotics.pdf on Aug. 11, 2004.
Campbell et al., "An Enteral Formula Containing Fish Oil, Indigestible Oligosaccharides, Gum Arabic and Antioxidants Affects Plasma and Colonic Phospholipid Fatty Acid and Prostaglandin Profiles in Pigs," Journal of Nutrition, vol. 127, No. 1, Jan. 1997, pp. 137-145.
Caplan et al., "Effect of Polyunsaturated Fatty Acid (PUFA) Supplementation on Intestinal Inflammation and Necrotizing Enterocolitis (NEC) in a Neonatal Rat Model," Pediatric Research, vol. 49, No. 5, 2001, pp. 647-652.
Carlson et al., "Lower Incidence of Necrotizing Enterocolitis in Infants Fed a Preterm Formula with Egg Phospholipds," Pediatric Research, vol. 44, issue 4, Oct. 1998, pp. 491-498.
Carver et al., "The role of nucleotides in human nutrition," J. Nutr. Biochem., vol. 6, Feb. 1995, pp. 58-72.
Cho et al., Complex Carbohydrates in Foods, Marcel Dekker Inc., NY, 1999, pp. 229-233, 146 (ISBN: 0-8247-0187-9).
Claud et al., "Hypothesis: inappropriate colonization of the premature intestine can cause neonatal necrotizing enterocolitis," The FASEB Journal, vol. 15, Jun. 2001, pp. 1398-1403.
CODEX STAN 72, "Standard for Infant Formula and Formulas for Special Medical Purposes Intended for Infants," 1981, pp. 1-21.
Connor et al., "Increased Docosahexaenoic Acid Levels in Human Newborn Infants by Administration of Sardines and Fish Oil During Pregnancy," Lipids, vol. 31, Supplement, 1996, pp. S-183-S-187.
Craig et al., "Polydextrose as Soluble Fiber: Physiological and Analytical Aspects," American Assn of Cereal Chemists, Inc., vol. 43, No. 5, May 1998, pp. 370-376 (publication No. W-1998-0427-03F).
Crittenden et al, "Production, properties and applications of food-grade oligosaccharides," Trends in Food Science & Technologies, vol. 7, Nov. 1996, pp. 353-361.
Cummings, "Gastrointestinal Effects of Food Carbodhydrate.sup.1-3," Am J Clin Nutr, Apr. 1995; Suppl. 4 61 (suppl): pp. 938S-945S.
Dairy Chemistry and Physics, University of Guelph, obtained from http://www.foodsci.uoguelph.ca/dairyedu/chem.html, Feb. 4, 2001, 16 pages.
Database CA 'Online! Chemical Abstracts Service, Columbus, Oh, NOGAMI, "Resin Compositions for low-temperature curable powder paints," retrieved from STN Database accession No. 87:137415 abstract & JP 53 042340 B, Nov. 10, 1978.
Database Medline [Online], US NLM, Dec. 1994, Malorni et al.: "Thiol supplier N-acetylcysteine enhances conjugate formation between natural killer cells and K562 or U937 targets but increases the lytic function only against the latter," Database accession No. NLM7721335, & Immunology Letters, vol. 43, No. 3, Dec. 1994, 1 page [XP002474080].
Database WPI Week 199633, Derwent Publications, Ltd., London, GB: AN 1996-329426 [XP-002426042].
Database WPI, Section Ch, Week 200261, Derwent Publications Ltd., London, GB, Class A26, AN 2002-567199 & CN 1 343 727 A, Apr. 10, 2002 [XP-002344565].
Database WPI, Section Ch. Week 198929, Derwent Publications Ltd., London, GB, Class B03, AN 1989-211474.
Database WPI, Section Ch. Week 199615, Derwent Publications Ltd., London, GB, Class B04, AN 1996-145913.
Database WPI, Week 200634, Derwent Publications Ltd., London, GB, AN 2006-323978 & JP 2006 115826 A, May 2006 [XP-002474081].
Detry, Dissertation, 1992, Institute Paul Lambin "Implications technologiques et nutritionelles . . . ".
Dombo et al., "Production Health Benefits and Applications of Galacto-oligosaccharides," Yalpani M. ed., New Technologies for Healthy Foods and Neutraceuticals, ATL Press, Shewsbury, MA, 1997, pp. 143-156.
Dongowski et al., "The Degree of Methylation Influences the Degradation of Pectin in the Intestinal Tract of Rats In Vitro." The Journal of Nutrition, vol. 132, 2002, pp. 1935-1944.
Droege et al, "Is AIDS the consequence of a virus-induced cysteine and glutathione deficiency? Chances and limitations of the treatment with N-acetyl-cysteine (NAC)," AIDS Research and Human Retroviruses, vol. 10, No. Suppl. 3, 1994, p. S65 (XP008052583).
Droege et al., "Glutathione and immune function," Proceedings of the Nutrition Society, vol. 59, No. 4, Nov. 2000, pp. 595-600.
Droege et al., "Role of cysteine and glutathione in HIV infection and other diseases associated with muscle wasting and immunological dysfunction," FASEB Journal, vol. 11, No. 13, Nov. 1997, pp. 1077-1089.
Droege, "Cysteine and glutathione deficiency in AIDS patients: A rationale for the treatment with N-Acetyl-Cysteine," Pharmacology (Basel), vol. 46, No. 2, 1993, pp. 61-65.
Elfstrand et al., "Immunoglobulins, growth factors and growth hormone in bovine colostrum and the effects of processing," International Dairy Journal, vol. 12, 2002, pp. 879-887.
Elix'or® "Galacto-oligosaccharides for Innovative Foods," Borculo Whey Products product information material, 1996.
Elix'or® "Galacto-oligosaccharides: A natural ingredient for functional foods," Borculo Whey Products product information brochure, Jul. 1996.
European Search Report dated Aug. 13, 2004, EP 1 597 978 A1, 4 pages.
Facchini et al., "Increased Number Of circulating Leu 11+ (CD 16) large granular lymphocytes and decreased NK activity during human ageing," Clinical Experimental Immunology, vol. 68, No. 2, 1987, pp. 340-347.
Fanaro et al., "Galacto-Oligosaccharides and Long-Chain Fructo-Oligosaccharides as Prebiotics in Infant Formulas: A Review," Acta Paediatrica Supplement, 94(449):22-26 (2005).
FAO Corporate Document, "The relationship between food composition and available energy," Provisional Agenda Item 4.1.3, Oct. 5-17, 1981, Rome, by D.A.T. Southgage, A.R.C. Food Research Institute, Norwich, UK, 10 pages.
Ferrandez et al., "Effects in vitro of several antioxidants on the natural killer function of aging mice—differing roles for IFN-

(56) References Cited

OTHER PUBLICATIONS gamma and IL-2," Experimental Gerontology, vol. 34, No. 5, Aug. 1999, pp. 675-685 [XP002474079].
FIBRULINE® Instant, Certificate of Analysis, Cosucra B.V., Netherlands, Oct. 12, 1994, 1 page.
Fidler et al., "Polyunsaturated fatty acid composition of human colostrum lipids in Slovenia: regional differences," Food Technology and Biotechnology, vol. 38, No. 2, 2000, pp. 149-153, Biotech. Fac., Inst. of Nutr., Univ. of Ljubljana, SI-1230 Domzale, Slovenia.
Fidler et al., "The fatty acid composition of human colostrum," European Journal of Nutrition, vol. 39, No. 1, Feb. 2000, pp. 31-37.
Fox, "Bovine Colostrum as a Resource for the Powerful Antioxicant Glutathione," Immune-Tree South Africa, Nov. 2008, pp. 1-7.
Frisomum, Analysis Chart and Brochure, 1998.
Ghoneum et al., "Enhancement of Natural Killer Cell Activity of Aged Mice by Modified Arabinoxylan Rice Bran (MGN-3/Biobran)," J. Pharm. and Pharmacology, vol. 56, No. 12, Dec. 2004, pp. 1581-1588.
Ghoneum et al., "Production of Tumor Necrosis Factor-Alpha and Interferon-Y from Human Peripheral Blood Lymphocytes by MGN-3, a Modified Arabinoxylan from Rice Bran, and its Synergy with Interleukin-2 In Vitro," Cancer Detection and Prevention, vol. 24, No. 4, 2000, pp. 314-324.
Gibson et al., "Dietary Modulation of the Human Colonic Microbiota: Introducing the Concept of Prebiotics," American Institute of Nutrition, 0022-3166, 1995, pp. 1401-1412.
Gibson et al., "Selective stimulation of bifidobacteria in the Human Colon by Oligofructose and Inulin," Gastroenterology, vol. 108, 1995, pp. 975-982.
Gibson, "Bifidogenic properties of different types of fructo-oligosaccharides," Food Microbiology, vol. 11, 1994, pp. 491-498.
Glade, Nutritional Pharmaceuticals "Conference Summary: First Symposium of the International College of Advanced Longevity Medicine, Reno, Nevada, Oct. 11-13, 1998," Nutrition, vol. 16, Issue 9, 2000, pp. 789-790.
Gonzalez et al., "Polysaccharides as Antiviral Agents: Antiviral Activity of Carrageenan," Antimicrobial Agents and Chemotherapy, vol. 31, No. 9, Sep. 1987, pp. 1388-1393.
Guggenbichler et al., "Acidic oligosaccharides from natural sources block adherence of *Escherichia coli* on uroepithelial cells," Pharm. Pharmacol. Lett., vol. 7, No. 1, Jun. 1997, pp. 35-38.
Haastrecht, "Oligosaccharides: Promising Performers in New Product Development," IFI, No. 1, 1995, pp. 23-27.
Hallert, C. et al. Scand. J. Gastroenterol., Ispaghula Husk May Relieve Gastrointestinal Symptoms in Ulcerative Colitis in Remission, 1991, vol. 26, No. 7, pp. 747-750.
Harmsen et al., "Analysis of Intestinal Flora Development in Breast-Fed and Formula-Fed Infants by Using Molecular Identification and Detection Methods," J. Pediatr. Gastroenterol. Nutr., vol. 30, 2000, pp. 61-67.
Hartemink "Non-digestible oligosaccharides: healthy food for the colon?," Proceedings of the International Symposium, Wageningen Pers, NL, Dec. 4-5, 1997, pp. 130-131 (ISBN 90-74134-52-1).
Hauer et al., "Mechanism of Stimulation of Human Natural Killer Cytotoxicity by Arabinogalactan from Laris Occidentalis," Cancer Immuno. Immunotherapy, vol. 36, No. 4, 1993, pp. 237-244.
Hendricks et al., "High-fiber diet in HIV-positive men is associated with lower risk of developing fat deposition"; Am J Clin Nutr, 2003; pp. 790-795.
Hertzler et al., "Colonic Adaptation to Daily Lactose Feeding in Lactose-Maldigesters Reduces Lactose-Intolerance," Am. J. Clin. Nutr., 1996, pp. 232-236.
Hirayama, "Novel physiological functions of oligosaccharides," Pure Appl. Chem., vol. 74, No. 7, 2002, pp. 1271-1279.
Hopkins et al., "Nondigestible Oligosaccharides Enhance Bacterial Colonization Resistance against Clostridium difficile In Vitro," Applied and Environmental Microbioloby, vol. 69, issue 4, Apr. 2003, pp. 1920-1927.
Igoe et al., Dictionary of Food Ingredients, 3rd Ed., Chapman and Hall, 1996, pp. 46, 66, 67, and 94.

Innovate with RAFTILINE® (ORAFTI leaflet), Nov. 1996.
Innovate with RAFTILOSE RAFTIMIX® (ORAFTI leaflet), Nov. 1996.
International Search Report dated Oct. 20, 2005, PCT/NL2005/000372, 3 pages.
Isolauri et al., "Probiotics in the management of atopic eczema," Clinical and Experimental Allergy, vol. 30, 2000, pp. 1604-1610.
Isolauri, E. et al., Clinical and Experimental Allergy, "Probiotics in the management of atopic eczema", 2000, vol. 30, pp. 1604-1610.
Ito et al., "Effects of Administration of Galactooligosaccharides on the Human Faecal Microflora, Stool Weight and Abdominal Sensation," Microbial Ecology in Health and Disease, vol. 3, No. 6, Nov.-Dec. 1990, pp. 285-292.
Ito et al., "Effects of Transgalactosylated Disaccharides on the Human Intestinal Microflora and Their Metabolism," J. Nutr. Sci. Vitaminol., vol. 39, 1993, pp. 279-288.
Ito et al., "Influence of Galactooligosaccharides on the Human Fecal Microflora," J. Nutr. Sci. VItaminol, vol. 39, 1993, pp. 635-640.
Ito et al., "Influence of Lactose on Faecal Microflora in Lactose Maldigestors," Microbial Ecology in Health and Disease, vol. 6, 1993, pp. 73-76.
Jacobson et al., "Absolute or total lymphocyte count as a marker for the CD4 T lymphocyte criterion for initiating antiretroviral therapy," AIDS (Hagerstown), vol. 17, No. 6, Apr. 11, 2003, pp. 917-919 (XP008052430).
Jenkins et al., "Inulin, Oligofructose and Intestinal Function," J. Nutrition, vol. 129, 1999, pp. 1431S-1433S.
Jiang et al., "In Vitro Lactose Fermentation by Human Colonic Bacteria is Modified by Lactobacillus Acidophilus Supplementation," American Society for Nutritional Sciences, 1997, pp. 1489-1495.
Jirapinyo et al., "HIV Disease: Working Group Report of the First World Congress of Pediatric Gastroenterology, Hepatology, and Nutrition," J. Ped. Gastroenterology and Nutrition, vol. 35, Aug. 2002, pp. S134-S142.
Kirjavainen, et al. "Characterizing the composition of intestinal microflora as a prospective treatment target in infant allergic disease", FEMS Immunology and Medical Microbiology (2001) vol. 32, pp. 1-7.
Kirk-Othmer, Encyclopedia of Chemical Technology, 4th Ed., vol. 12, 1994, pp. 855-856.
Kleessen et al., "Fructans in the diet cause alterations of intestinal mucosal architecture, released mucins and mucosa-associated bifidobacteria in gnotobiotic rats," British Journal of Nutrition, vol. 89, 2003, pp. 597-606.
Klose et al., "Gums," CRC Handbook of Food Additives, Chpt. 7, 2nd Ed., 1972, pp. 305-307.
Kohmoto et al., "Effect of Isomalto-oligosaccharides on Human Fecal Flora," Bifidobacteria microflora, vol. 7, No. 2, 1988, pp. 61-69.
Koletzko et al., "Growth, development and differentiation: a functional food science approach," British Journal of Nutrition, vol. 80, Suppl. 1, 1998, pp. S5-S45.
Kulkarni et al., "Immunostimulant activity of inulin isolated from Saussurea lappa roots," Indian Journal of Pharmaceutical Sciences, vol. 63, No. 4, Jul. 2001, pp. 292-294.
Laidlaw et al., "Effects of supplementation with fish oil-derived n-3 fatty acids and (-linolenic acid on circulating plasma lipids and fatty acid profiles in women," Am J Clin Nutr, vol. 77, 2003, pp. 37-42.
Listing of sales of RAFTIMIX® 10 to clients i.a. in period Sep. 13, 1996 to May 19, 1998.
Manufacture protocol with composition of RAFTIMIX® 10 1995.
Marini et al., "Pro- and pre-biotics administration in preterm infants: colonization and influence on faecal flora," Acta Paediatrica Scandinavica Supplement, 92(441):80-81 (2003) (Abstract Only).
Marshall, "Therapeutic Applications of Whey Protein," Alternative Medicine Review, vol. 9, No. 2, 2004, pp. 136-156.
Marteau et al., "Nutritional advantages of probiotics and prebiotics," British Journal of Nutrition, vol. 87, Sup. 2, 2002, pp. S153-S157.
Martin-Sosa et al., "Sialyloligosaccharides in Human and Bovine Milk and in Infant Formulas: Variations with the Progression of Lactation," Journal of Dairy Science, 86:52-59 (2003).

(56) References Cited

OTHER PUBLICATIONS

Mata et al., "Evaluation of a recombinant Listeria monocytogenes expressing an HIV protein that protects mice against viral challenge," Vaccine, vol. 19, 2001, pp. 1435-1445.
MayoClinic.com "prevention of HIV/AIDS," 4 pages, also available at http://www/mayoclinic.com/health/hiv-aids/DS00005/DSECTION=prevention, last viewed Aug. 21, 2009.
MayoClinic.com, "Ulcerative colitis,"13 pages, also available at http://www/mayoclinic.com/health/ulcerative-colitis/DS00598/METHOD=print&DSECT . . . , last viewed Nov. 24, 2010.
McGraw-Hill Access Science Encyclopedia of Science & Technology Online "acid," also available at http://www.accessscience.com/content.aspx?searchStr=acid&id=004400#004400s004, last viewed Aug. 21, 2009.
McGraw-Hill Access Science Encyclopedia of Science & Technology Online "oligosaccharide," also available at http://www.accessscience.com/content.aspx?searchStr=oligosaccharide&id=468300, last viewed Aug. 21, 2009.
McGraw-Hill Access Science Encyclopedia of Science & Technology Online "Acid and Base," also available at http://www.accessscience.com/content.aspx?searchStr=acid&id=004400, last viewed Aug. 20, 2009.
Meleghi et al., "New baby food milk products," XXI International Dairy Congress brief communications, vol. 1, book 2, Moscow, Jul. 12-16, 1982, p. 128.
Merck Manual, "Atopic and Allergic Disorders," also available at http://www.merck.com/mmpe/sec13/ch165/ch165c.html?qt=allergy&alt=sh#sec13-ch165-ch165c-319, last viewed Mar. 16, 2010.
Meslin et al., "Effects of galacto-oligosaccharide and bacterial status on mucin distribution in nucosa and on large intestine fermentation in rats," British Journal of Nutrition, vol. 69, 1993, pp. 903-912.
Miniello et al., "Prebiotics in infant milk formulas: New Perspectives," Acta Paediatrica Suppl., 441, 2003, pp. 68-76.
Mitsuoka, "Intestinal Flora and Human Health," Asa Pacific J. Clin. Nutr., vol. 15, 1996, pp. 2-8.
Mizota et al., "Lactulose as a Sugar with Physiological Significance," Bulletin IDF, No. 212, Trends in Whey Utilization, 1987, chapter 11, session III, pp. 69-76.
Mori et al., "Effects of Glycyrrhizin (SNMC: Stronger Neo-Minophagen C) in hemophilia patients with HIV-1 Infection," Tohoku J. Exp. Med., vol. 162, No. 2, 1990, pp. 183-193.
Moro et al., "Dosage-Related Bifidogenic Effects of Galacto- and Fructooligosaccharides in Formula-Fed Term Infants," Journal of Pediatric Gastroenterology and Nutrition, (Mar. 2002), vol. 34, No. 3, pp. 291-295.
Moro et al., "Effects of a new mixture of prebiotics on faecal flora and stools in term infants," Acta Paediatrica Suppl., vol. 91, No. 441, Sep. 2003, pp. 77-79.
Moro et al., "Reproducing the bifidogenic effect of human milk in formula-fed infants: Why and how?" Acta Paediatrica Suppl., 449, vol. 94, 2005, pp. 14-17.
Murphy, "Non-Polyol Low-Digestible Carbohydrates: Food Applications and Functional Benefits," British Journal of Nutrition, vol. 85, suppl. 1, 2001, pp. S47-S53.
Nakano et al., "Anti-Human Immunodeficiency Virus Activity of Oligosaccharides from Rooibos Tea (*Aspalathus linearis*) Extracts in Vitro," Leukemia, vol. 11, No. suppl. 3, Macmillan Press Ltd., US, 1997, pp. 128-130.
ORAFTI "inulin," also available at http://www.orafti.com/Our-Products/Inulin, last viewed Mar. 15, 2010.
Parcell, "Sulfur in Human Nutrition and Applications in Medicine," Alternative Medicine Review, vol. 7, No. 1, Feb. 2002, pp. 22-24, Thorne Research Inc., Sandpoint, US.
Patent Abstracts of Japan, vol. 013, No. 408 (C-634), Sep. 8, 1989 (JP 01 149730 A, Jun. 12, 1989).
Patent Abstracts of Japan, vol. 017, No. 119 (C-1034), Mar 12, 1993 (JP 04 300888 A, Oct. 23, 1992).
Plettenberg et al., "A preparation from bovine colostrum in the treatment of HIV-positive patients with chronic diarrhea," Clinical Investigator, vol. 71, 1993, pp. 42-45.
ProBLEN Anti-Aging Supplements, "Digestive Enzyme with Probiotics," Brochure dated Aug. 20, 2010, 4 pages.
RAFTILINE® HP Product Sheet Release: May 1995.
RAFTILINE® ST Product Sheet Release: May 1995.
RAFTILOSE® P95 Product Sheet Release: May 1995.
RAFTIMIX® 10 Product Sheet Release: May 1995.
Reddy et al., "Effect of dietary oligofructose and inulin on colonic preneoplastic aberrant crypt foci inhibition," Carcinogenesis, vol. 18, No. 7, 1997, pp. 1371-1374.
Reich et al., "Tonicity, Osmoticity, Osmolality, and Osmolarity," Remington: The Science and Practoce of Pharmacy, 20th ed., 2000, pp. 246-256.
Rigo et al,. "Growth, Weight Gain Composition and Mineral Accretion in Term Infants Fed a New Experimental Formula Containing Hydrolysed Protein, Beta-Palmitate and Prebiotics," Pediatrika, Alpe, Madrid, Spain, vol. 21, No. 10, 2001, pp. 387-396.
Roberfroid et al., "The Bifidogenic Nature of Chicory Inulin and its Hydrolysis Products," Journal of Nutrition, vol. 128, 1998, pp. 11-19.
Roberfroid et al., "Health Benefits of Non-Digestible Oligosaccharides," NCBI Pub Med, 1997.
Roberfroid, "Dietary Fiber, Inulin, and Oligofructose: a review comparing their physuikigucak effects," Critical Reviews in Food Science and Nutrition, vol. 33, No. 2, 1993, pp. 103-148.
Roberfroid, "Prebiotics: preferential substrates for specific germs?," Am J. Clin. Nutr., vol. 73 (suppl), 2001, pp. 406S-409S.
Roman et al., "Original Communication Nutritional treatment for acquired immunodeficiency virus infection using an enterotropic peptide-based formula enriched with n-3 fatty acids: a randomized prospective trial," European Journal of Clinical Nutrition, vol. 55, 2001, pp. 1048-1052.
Rotimi et al, "The Development of the Bacterial Flora in Normal Neonates," J. Med. Microbiol., vol. 14, 1981, pp. 51-62.
Rubaltelli et al., "Intestinal Flora in Breast- and Bottle-fed Infants," J. Perinant. Med., vol. 26, 1998, pp. 186-191.
Salminen et al., "Functional food science and gastrointestinal physiology and function," British Journal of Nutrition, vol. 80, suppl. 1, 1998, pp. S147-S171.
Sansoni, "Lymphocyte Subsets and Natural Killer Cell Activity in Healthy Old People and Centenarians," Blood, vol. 82, No. 9, Nov. 1, 1993, pp. 2767-2773.
Schley, P.D. et al., British Journal of Nutrition, The immune-enhancing effects of dietary fibres and prebiotics, 2002, vol. 87, Supplement S2, pp. S221-S230.
Schmelzle, H. et al. "Randomized Double-Blind Study of the Nutritional Efficacy and Bifidogenicity of a New Infant Formula Containing Partially Hydrolyzed Protein, a High beta-Palmitic Acid Level, and Nondigestible Oligosaccharides", Journal of Pediatric Gastronenterology and Nutrition, Mar. 2003, vol. 36, pp. 343-351.
Simopoulos et al., "Workshop on the Essentiality of and Recommended Dietary Intakes for Omega-6 and Omega-3 Fatty Acids", Journal of the American College of Nutrition, vol. 18, No. 5, 1999, pp. 487-489.
Stockman et al., "Mechanisms of Epithelial Barrier Impairment in HIV Infection," Annals New York Academy of Sciences, 2000 pp. 293-303.
Szilagyi, "Review article: lactose—a potential prebiotic," Ailment Pharmacol Ther, vol. 16, 2002, pp. 1591-1602.
Tanaka et al., "Effects of Administration of TOS and Bifodobacterium breve 4006 on the Human Fecal Flora," Bifidobacteria Microflora, vol. 2, No. 1, 1983, pp. 17-24.
Terada et al., "Effect of Lactosucrose on Fecal Flora and Fecal Putrefactive Products of Cats," NCBI PubMed, 1993.
Think RAFTILINE®, RAFTILOSE®, Inuline and Oligofructose, (Orafti brochure), Apr. 23, 2008.
Usami et al., "Effect of Eicosapentaenoic Acid (EPA) on Tight Junction Permeability in Intestinal Monolayer Cells," Clinical Nutrition, 2001, vol. 20(4), pp. 351-359.
Van Laere et al., "Mogelijkheden en toepassingen van prebiotica: Possibilities and applications of prebiotics," Voedingsmiddelen

(56) References Cited

OTHER PUBLICATIONS

Technologie, Noordervliet B.V. Zeist, NL, vol. 34, No. 23, Oct. 26, 2001, pp. 51-54 (XP008029566; ISSN: 0042-7934).

Van Loo et al., "On the Presence of Inulin and Oligofructose as Natural Ingredients in the Western Diet," Critical Reviews in Food Science and Nutrition, vol. 35, No. 6, 1995, pp. 525-552.

Watanabe et al., "Therapeutic Effects of Glycyrrhizin in Mice Infected with LP-BM5 Murine Retrovirus and Mechanisms Involved in the Prevention of Disease Progression," Biotherapy, vol. 9, No. 4, 1996, pp. 209-220, Kluwer Academic Publishers, Dordrecht, NL.

Watzl et al., "Inulin, oligofructose and immunomodulation," British Journal of Nutrition, vol. 93, No. 1, 2005, pp. S49-S55 [XP002474088].

Wilcox, C.M., Rabeneck, L., Friedman, S. (1996) AGA Technical Review; Malnutrition and Cachexia, Chronic Diarrhea, and Hepatobiliary Disease in Patients with Human Immunodeficiency Virus Infection. Gastroenterology, vol. 111, p. 1724-1752.

Willemsen et al., "Short chain fatty acids stimulate epithelial mucin 2 expression through differential effects on prostaglandin E1 and E2 production by intestinal myofibroblasts," www.gutinl.com, 2003, pp. 1442-1447.

WordNet "prevent"; also available at http://wordnetweb.princeton.edu/perl/webwn?s=prevent&o2=&o0=1&o7=&o5=&o1=1&o6=&o4=&o3=&h=, last viewed Aug. 24, 2009.

Yazawa et al., "Search for Sugar Sources for Selective Increase of Bifidobacteria," Bifidobacteria microflora, vol. 1, No. 1, 1982, pp. 39-44.

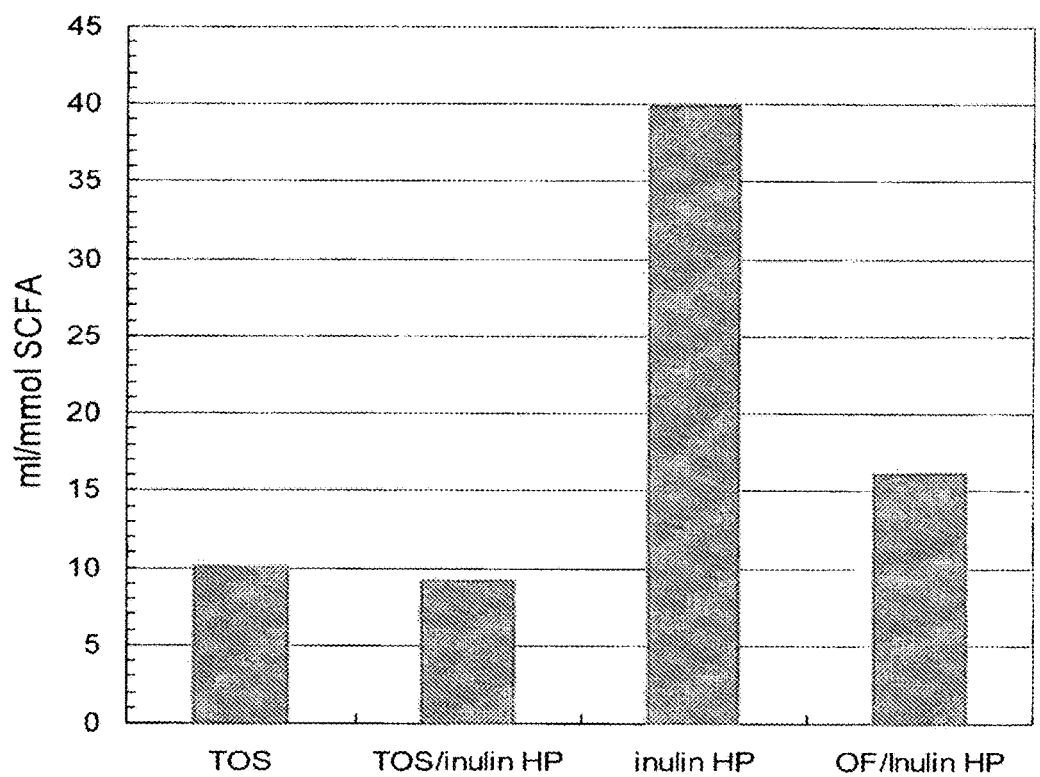

SYNERGISM OF GOS AND POLYFRUCTOSE

CROSS-REFERENCE TO RELATED APPLICATIONS

This application is a Continuation of U.S. patent application Ser. No. 13/750,749, filed Jan. 25, 2013, which is a Continuation of U.S. patent application Ser. No. 11/569,239, filed Jan. 16, 2008, which is the National Phase of International Patent Application No. PCT/NL2005/000372, filed May 17, 2005, which claims priority to European Patent Application No. 04076479.7, filed May 17, 2004. The contents of these applications are herein incorporated by reference in their entirety.

FIELD OF THE INVENTION

The present invention relates to the field of human health and nutrition. It provides novel synergistic mixtures of prebiotic carbohydrates, especially mixtures of galacto-oligosaccharides (GOS, for example TOS) and polyfructose (for example inulin), as well as nutritional compositions comprising these. The nutritional compositions have beneficial effects when fed to bottle fed or partially bottle fed infants and also have health improving effects when ingested by adults having intestinal problems, such as Inflammatory Bowel Disease (IBD) or Irritable Bowel Syndrome (IBS).

BACKGROUND OF THE INVENTION

The microflora of the human large intestine (typically divided into caecum, colon and rectum) plays a crucial role in both human nutrition and health. The bacterial composition is influenced and can be modulated by dietary intake. Carbohydrates which have passed through the stomach and small intestine are metabolised by the bacteria and as a major end-product of metabolism short-chain fatty acids (SCFA), such as acetate, propionate, butyrate and valerate, are formed, which are subsequently released into the blood. Other end products of bacterial fermentation include for example lactate and succinate. The total amounts and compositions (relative amounts) of these end products in turn have a profound effect on bacterial growth, pH, exclusion of pathogenic species, etc. A method to beneficially influence the microbial flora and human health is the administration of prebiotics. "Prebiotics" were defined as "non-digestible food ingredients that beneficially affect the host by selectively stimulating the growth and/or activity of one or a limited number of bacteria in the colon, and thus improve the hosts health (Gibson and Roberfroid 1995, J. Nutr. 125, 1401-1412). The criteria which a compound must fulfil in order to be classified as a prebiotic are: 1) it must not be hydrolysed or absorbed in the upper part of the gastrointestinal tract (stomach, small intestine), 2) it must be selectively fermented by one or more potentially beneficial bacteria in the colon, 3) it must alter the colonic microbiota towards a healthier composition and 4) it must preferably induce effects which are beneficial to the health of the subject. Commonly used prebiotics are so-called non-digestible carbohydrates (or "soluble dietary fibres"), which pass undigested through the upper part of the gastrointestinal tract into the large intestine. These include for example fructooligosaccharides (FOS), oligofructose, inulin and transgalactooligosaccharides (TOS). It should be noted that in the literature, there is often inconsistency between the use of various terms, such as fructooligosaccharide, inulin, oligofructose and inulo-oligosaccharides, and the same term may be used for different compounds or compositions.

Well known beneficial bacteria, which are stimulated by the uptake of prebiotics, are lactic acid bacteria, such as Lactobacilli and Bifidobacteria, and health benefits have been ascribed to be due to this stimulatory effect. For example, beneficial effects of inulin and inulin-type fructans, such as oligofructose, on intestinal function have been described (Jenkins et al. 1999, J. Nutrition 129, 1431S-1433S) and this effect is thought to be due to a bifidogenic effect, which refers to a selective growth stimulating effect on total bifidobacteria, measured either in vivo through bifidobacterial counts of the faeces or in vitro (see e.g. Roberfroid, Am J Clin Nutr 2001, 73(suppl), 406S-409S).

Human milk appears also to have a bifidogenic effect, as the dominant bacteria which become established in breast-fed infants are bifidobacteria. In contrast, bacterial colonisation of milk formula fed infants is not dominated by bifidobacteria and is more diverse in bacterial species (Harmsen et al. 2000, J. Pediatr. Gastroenterol. Nutr. 30, 61-67). It is thought that oligosaccharides found in the human milk are responsible for the bifidogenic or prebiotic effect and efforts have been made to modify infant formula in such a way that it resembles human milk as closely as possible and especially that it has the same or a very similar prebiotic effect as human milk. This has been done by adding prebiotics to infant milk formula (Boehm et al. Acta Paediatr. Suppl. 2003, 441, 64-67 and Moro et al. 2002, J Pediatr Gastroenterol Nutr 34, 291-295). For example, supplementation of bovine milk formula with an oligosaccharide mixture comprising trans-galactooligosaccharides (TOS) and inulinHP has been described to increase the faecal count of bifidobacteria in bottle fed infants (Boehm et al. 2002, Arch Dis Child 86, F178-F181).

Also, supplementation of infant milk formula with TOS and inulin has been described to have a bifidogenic effect, and to decrease faecal pH (Boehm et al. 2003 supra; Moro et al. 2003, Acta Paediatr. Suppl. 441:77-79; Marini et al. 2003, Acta Paediatr. Suppl. 441:80-81; Boehm et al. 2002, Arch. Dis. Child Fetal. Neonata. Ed. 86:F178-F181; Moro et al. 2002, J. Pediatr. Gastroenterol. Nutr. 34:291-295; Schmelzle et al. 2003, J Pediatr. Gastroenterol. Nutr. 36:343-51).

Upon fermentation of prebiotics by lactic acid bacteria organic acids are produced and the pH is lowered. Lactobacilli produce either lactate or lactate and acetate (a Short Chain Fatty Acid; SCFA). The lactate can be in the L- or D-form. Bifidobacteria, on the other hand, produce L-lactate and acetate, but no D-lactate. Bifidobacteria (and other lactic acid bacteria) usually do not lead to the production of gases, such as $H_2$ and $CH_4$. They also do not produce other SCFA, such as propionate, butyrate, isobutyrate, valerate and isovalerate. The presence of SCFA, such as isobutyrate and isovalerate, are indicative of the fermentation of carbohydrates by other bacterial species, such as Clostridia and *Bacteroides* or Enterobacteriaceae, or are indicative for the fermentation of proteins (of which the Bifidobacteria have a poor capability). Also, other intestinal bacteria are capable of producing acetate or lactate, such as Propionibacteria, Enterococci and Pediococci.

Previously it has been reported that the intake of certain prebiotic carbohydrates increase the (relative) amounts of Bifidobacteria and/or Lactobacilli. Concomitantly an increased formation of SCFA and decrease of pH has been observed. But also the formation of gases, which results in unwanted symptoms such as flatulence and abdominal pain, has been reported when introducing prebiotics, such as inulin or GOS, into the diet. Furthermore, not only acetate but also increases in, for example, butyrate have been reported, which is undesirable. A range of undesirable effects have therefore been described, resulting from the consumption of nutrition supplemented with certain prebiotics.

In the colon and faeces of breast fed infants the predominant SCFA found is acetate. Furthermore high concentrations of lactate are found. These (relative) amounts are higher than those observed in adults (where concentrations of lactate are generally negligible) or in standard milk formula fed infants. Subsequently, concentrations of propionate and especially butyrate are much lower in the colon and faeces of breast fed infants than in adults and even lower than in infants fed with standard infant milk formula. The pH of the faeces is lowest in breast fed children. As mentioned above, it is desirable to provide nutrient compositions, especially milk formula compositions, which, when consumed, result in an intestinal microflora closely resembling that of breast fed infants.

Many health effects of SCFA and lactate and a low colon pH have been described. The lowered pH and the presence of organic acids have been described to have an antipathogenic effect, and provide an advantage to acid tolerant bacteria such as the lactic acid bacteria (including Bifidobacteria). Also effects of SCFA on the intestinal wall have been described. SCFA are an energy source of colonocytes and thereby aid to the intestinal barrier integrity. SCFA are also involved in effects on peristalsis, bile acid metabolism, water absorption and cell differentiation (see e.g. EP1105002). SCFA are known to stimulate the production of mucus and are involved in mineral absorption and mucus production.

DETAILED DESCRIPTION OF THE INVENTION

The present inventors surprisingly found that GOS (especially TOS) and polyfructose (especially inulin), when administered together, provide a number of beneficial effects which cannot be explained by an increase in the number of intestinal bifidobacteria and which are, therefore, not due to the bifidogenic effect described for TOS or inulinHP in the prior art (e.g. in Boehm et al. 2002, supra). In particular, it was unexpectedly found that, following administration of GOS and polyfructose mixtures, there was an increase in the total amounts of SCFA formed, an increase in the relative amounts of acetate and lactate and a decrease in faecal pH of infants, whereby these effects were not correlated with an increased (relative) amount of Bifidobacteria. Beside a beneficial SCFA amount and profile and an increased amount of lactate, a decrease in gas formation was observed. Further, lactate itself was found to have a hitherto unknown beneficial effect on the colon, as it was found to increase the secretion of prostaglandin E1 and prostaglandin E2. This effect was previously only reported for SCFA, especially acetate (Willemsen et al. 2003, Gut 52, 1442-1447). Compositions comprising lactate, and compositions comprising prebiotics which stimulate lactate production, may therefore be used to stimulate mucin production and support the mucosal barrier integrity (mucoprotection). Lactate was further found to decrease spontaneous contractions and tension in colonic muscles, resulting in relief of cramp and pain.

The prebiotic compositions are therefore novel, in that they do not, or do not significantly, increase the number of Bifidobacteria, while they do result in an increase in total SCFA amounts, beneficial changes in SCFA profile (increases in acetate, decreases in butyrate and propionate), increase in lactic acid (and resulting beneficial contraction and tension reducing effects and muco-stimulatory effect), a decrease in faecal pH, a decrease in formation of gases, and more gradual formation of SCFA (including formation in the distal part of the colon), i.e. overall an optimal pattern of fermentation products (more L-lactate, less butyrate etc.). All these changes make the colonic environment more resemble that of breast fed babies. In one embodiment of the invention the use of mixtures of GOS and polyfructose in effective amounts for the preparation of compositions which lead to a colonic environment essentially similar to that of breast fed infants is, therefore, provided herein.

The beneficial effects found were significantly more pronounced upon co-administration than when either GOS or polyfructose (e.g. TOS or inulin) alone was administered, indicating that GOS and polyfructose act synergistically. In the prior art no studies were carried out wherein the individual effects of TOS and inulin administration were directly compared to the co-administration of these two types of compounds and clearly such independent individual studies cannot be compared to one another and are unsuitable to identify synergistic effects.

This novel synergistic interaction of GOS and polyfructose (e.g. TOS and inulin), and the in vivo effects of co-administration thereof, leads to new uses of compositions comprising both GOS and polyfructose in suitable (synergistic) amounts, such as treatment or prevention of colic and/or abdominal cramps, abdominal bloating, flatulence, abdominal pain, constipation, IBS, IBD, allergy and/or increased mucoprotection of the intestine. In addition, a composition comprising lactate (D-lactate and/or L-lactate, preferably L-lactate) may be used to treat or prevent one or more of these symptoms or disorders.

Thus, unexpectedly, fermentation of the specific mixtures of prebiotics (GOS and polyfructose) by the intestinal flora results in an enhanced and kinetically advantageous formation of SCFA and lactate and an improved pattern of metabolic end products. As a consequence many beneficial effects result, such as effects on mucus production, anti-inflammatory effects, effects on pain perception and effects on abdominal cramps/colic (both via relaxation of the colon and decrease of spontaneous contractions). The nutrition compositions comprising these prebiotic mixtures can also be used for adults having intestinal problems such as IBD or IBS or a decreased intestinal barrier integrity due to malnutrition.

Definitions

"Polysaccharides" refers to carbohydrate chains of monosaccharide units with a chain length of at least 10 units. In contrast, "oligosaccharides" have a chain length of less than 10 units.

"Degree of polymerisation" or "DP" refers to the total number of saccharide units in an oligo- or polysaccharide chain. The "average DP" refers to the average DP of oligosaccharides or polysaccharide chains in a composition, without taking possible mono- or disaccharides into account (which are preferably removed if present). The average DP of a composition is used to distinguish between compositions. In addition the % saccharide units, such as the % glucose and % fructose units, in a composition are distinguishing.

"Polyfructose" or "polyfructan" or "fructopolysaccharide" refers to a polysaccharide carbohydrate comprising a chain of β linked fructose units with a degree of polymerisation of 10 or more and comprises, for example, inulin (e.g. inulin HP), levan and/or a "mixed type of polyfructan" (see below).

"Inulin" or "non-hydrolysed inulin" or "inulin HP" is used herein to refer to glucose-terminated fructose chains with the majority of chains (at least 90%, preferably at least 95%) having a degree of polymerisation (DP) of 10 or more. Inulin can thus be described as $GF_n$, wherein G represents a glucosyl unit, F represents a fructosyl unit and n is the number of fructosyl units linked to each other, n being 9 or more. The G/F ratio is about 0.1 to 0. A small part of the inulin molecules, however, may have no terminal glucose unit. The average DP is preferably at least 15, more preferably 20 or more, such as 20, 21, 22, 23, 25, 30, 40, 60, 70, 100, 150 or more herein. In inulin the fructose units are linked with a $\beta(2\rightarrow1)$ linkage. A suitable inulin is for example the commercially available as Raftiline®HP (Orafti) with an average DP>23.

"Hydrolised inulin" or "oligofructose" refers to mixtures of glucose- and fructose-terminated fructose chains, with a DP below 10. Thus, hydrolysed inulin can be described as a mixture of $GF_n$ chains and $F_n$ chains (wherein G is a glucosyl unit, F is fructosyl unit and n=1-8). Hydrolysed inulin is an (enzymatic or acidic) hydrolysis product or partial hydrolysis product of inulin, resulting from cleavage of β(1-2) fructosyl-fructose linkages. The term hydrolysed inulin also encompasses synthetically made or recombinantly made inulin which have the same structural makeup.

"Levan" or "levulan" or "levulin" or "levulosan" refers to a polysaccharide consisting of polyfructose in which the fructose units are linked with $\beta(2\rightarrow6)$ linkages. A starting glucose moiety can be present, but this is not necessary. The degree of polymerisation is above 10.

In "mixed type polyfructans" the fructose units are linked with $\beta(2\rightarrow1)$ and $\beta(2\rightarrow6)$ linkages. Mixed type polyfructans are branched and have a DP>10.

"GOS" or "galactooligosaccharides", or "trans-galactooligosaccharides" or "TOS" refers to oligosaccharides composed of galactose units, with a DP of 10 or less and an average DP of 2, 3, 4, 5 or 6. A glucose unit may be present at the reducing end of the chain. Preferably the GOS contains at least ⅔ galactose units. Most preferred are trans-galactooligosaccharides (TOS) with β-(1-4) glycosidic bonds. Such a GOS is for example that found in Vivinal®GOS (commercially available from Borculo Domo Ingredients, Zwolle, Netherlands), comprising trans-galactooligosaccharides with β-(1-4) glycosidic bonds and β-(1-6) glycosidic bonds.

"SCFA" or "short chain fatty acids" refers to fatty acids, with a carbon chain lengths of up to C6, produced as an end-product of bacterial intestinal fermentation, such as acetate (C2), propionate (C3), butyrate and isobutyrate (C4), valerate and isovalerate (C5) and others The expression "iC4-5" refers to the sum of isobutyrate, valerate and isovalerate.

A "synergistically effective amount" refers to an amount of GOS and polyfructose (for example TOS and inulin) which, when co-administered, confers one (or more) specific physiological effects (as described elsewhere herein), whereby the total effect of co-administration is significantly larger than the sum of the effect of individual administration of GOS or polyfructose. For example, if the effect of administration of GOS alone is X and the effect of administration of polyfructose alone is Y, then the effect of co-administration of GOS and polyfructose is larger than X+Y and for example the effect of co-administration of ½ the concentration of GOS plus ½ the concentration of polyfructose has an effect larger than ½ X+½ Y, etc.

"Co-administration" of two or more substances refers to the administration of these substances to one individual, either in one composition or in separate compositions (kit of parts; as a combined composition) which are administered at the same time (simultaneously) or within a short time-span (separate or sequential use, e.g. within minutes or hours).

"Enteral" refers herein to the delivery directly into the gastrointestinal tract of a subject (e.g. orally or via a tube, catheter or stoma).

The term "comprising" is to be interpreted as specifying the presence of the stated parts, steps or components, but does not exclude the presence of one or more additional parts, steps or components.

"Infant" refers herein to humans aged 0-36 months, preferably 0-18 months, or more preferably 0-12 months.

"Breast fed infants" refers to infants exclusively fed with human breast milk. "Non- or partially breast fed infants" are infants not exclusively fed on human breast milk. This includes infants fed with at least one bottle (about 80 ml) of formula milk per day.

"Percentage" or "average" generally refers to percentages of averages by weight, unless otherwise specified or unless it is clear that another basis is meant.

In one embodiment the present invention provides a number of novel uses of compositions comprising both GOS and polyfructose in suitable (synergistically effective) amounts.

Uses and Methods According to the Invention

In the various uses described herein, a subject is preferably a human subject, more preferably an infant, such as a new born infant up to a 12 months old infant. Especially bottle fed or partially bottle fed infants are referred to. Alternatively, a subject may also be a child, teenager or adult. In particular intestinal problems, such as but not limited to Inflammatory Bowel Disease (IBD), Irritable Bowel Syndrome (IBS), flatulence, abdominal cramps, colic, abdominal bloating, abdominal pain, etc., which may also result in fatigue, depression or moodiness, may be prevented and/or treated using compositions according to the invention. Also, mucosal production may be enhanced and allergies resulting from a suboptimal functioning of the intestine may be prevented or treated. Also the intestinal barrier function may be improved in patients with an impaired barrier function as a result from malnutrition, surgery, chemotherapy etc.

Compositions comprising both GOS and polyfructose, such as compositions comprising TOS and inulin, may in one embodiment be used to induce the production of SCFA in the large intestine of a subject and to significantly increase the (intestinal and/or faecal) total amount of SCFA produced following administration and/or to significantly modify the relative amounts of (intestinal and/or faecal) SCFA produced, in particular to increase the (intestinal and/or faecal) relative amount of acetate out of total SCFA, and/or to significantly increase the amount (absolute and relative) of intestinal lactate produced, and/or to significantly reduce or prevent intestinal gas formation, and/or to extend the SCFA production to the distal part of the colon, and/or to significantly reduce the pH in the large intestine and faecal pH. Also, the sum of intestinal and/or faecal butyrate, isobutyrate, valerate and/or isovalerate relative to the total SCFA may be decreased. These effects are achieved following administration, without having a significant effect on the total and/or relative number of intestinal bifidobacteria. Compositions for the treatment or prophylaxis of any diseases or disorders or discomforts associated with or caused by one or more of these intestinal effects are provided herein.

The present invention provides the use of galacto-oligosaccharides and polyfructose for the manufacture of a composition for the treatment or prevention of abdominal bloating, gas formation, abdominal pain and/or flatulence. In a further embodiment the present invention provides the use of galactooligosaccharides and polyfructose for the manufacture of a composition for the treatment or prevention of allergy, eczema or atopic diseases. In a further embodiment the present invention provides the use of galacto-oligosaccharides and polyfructose for the manufacture of a composition for the treatment and/or prevention of colics and/or for the relaxation of contractions of the colon, preferably the tonic and/or phasic contraction. In another embodiment the present invention provides the use galacto-oligosaccharides and polyfructose for the manufacture of a composition for the treatment or prevention of irritable bowel syndrome or inflammatory bowel disease. In an even further embodiment the present invention provides the use of galacto-oligosaccharides and polyfructose for the manufacture of a composition for the increase of intestinal barrier functioning and/or mucus production in the large intestine.

Unless specified otherwise, a "significant increase" (of for example SCFA, acetate or lactate) refers herein to an increase of at least 5%, preferably at least 10%, more preferably at least 20%, or more, compared to the amount produced when either GOS or polyfructose (e.g. inulin) alone are administered. Similarly, unless specified otherwise a "significant reduction" (of for example gas formation) refers to a reduction of at least 5%, preferably at least 10%, more preferably at least 20%, 25%, 50% or more (e.g. 70%, 80%, 90%, 100%) compared to the amount produced when polyfructose (e.g. inulin) alone is administered.

An increase in the total amount of SCFA produced as fermentation product of GOS and polyfructose compositions can also be measured as a significant decrease in pH of faecal samples of subjects, reflecting an in vivo decrease in pH in the large intestine. In infants it was found that faecal pH decreased to about pH 5.8 or less, such as pH 5.6, 5.5 or 5.4 or 5.2 following co-administration of TOS and polyfructose (e.g. inulin), while the pH of standard formula fed infants was around or above pH 6, such as about pH 5.9, 6.8 or even 7.0. A significant decrease in pH refers therefore to a decrease in pH by at least 15% or 0.9 unit compared to infants fed a standard formula.

Another beneficial effect of co-administration of GOS and polyfructose in suitable amounts is that the composition of SCFA is significantly different than when either GOS or polyfructose are administered. Especially the relative amount of butyrate is significantly reduced, while the relative amount of acetate is significantly increased. The compositions may, thus, be used to alter not only total SCFA quantities, but also relative SCFA proportions. In infants co-administered with TOS and polyfructose (e.g. inulin), the relative SCFA levels resembled more the levels found in breast fed infants, with acetate:propionate:butyrate ratios generally about 80-85%:10-15%:1-5%, while in infants fed on standard milk formula ratios were generally around 69-74%:16-19%:5-6% (as shown in the examples). Thus, especially relative amounts of acetate are increased and relative amounts of propionate and butyrate are decreased by the compositions according to the invention. The co-administration of GOS and polyfructose results in acetate:propionate:butyrate proportions resembling that of breast-fed infants much more closely than that of formula fed infants (which produce high levels of butyrate and propionate and relatively low levels of acetate). The effect on relative SCFA proportions can be measured by methods known in the art, such as gas chromatography of faecal samples at various time points after administration, either using in vivo studies or an in vitro fermentation systems as e.g. described in the Examples. A "significantly modified SCFA composition" or a "significantly increased amount of acetate" refers to the amount of acetate (% of total SCFA) being at least about 4%, 5%, 10%, 15%, or more, higher than when no GOS or polyfructose are administered or when GOS or polyfructose are administered individually. Preferably the relative amounts of propionate and/or butyrate are lower than when no GOS or polyfructose are administered or when GOS or polyfructose are administered individually. In one embodiment, the composition according to the invention is suitable for increasing intestinal and/or faecal acetate to above about 85%, such as 86%, 87%, 88%, 90% or more, of the total SCFA.

Yet a further beneficial effect observed when co-administering GOS and polyfructose is a significant decrease in branched SCFA, compared to the proportion of branched SCFA found when only GOS or only polyfructose are administered. A "significant decrease in branched SCFA", as used herein, refers to a decrease at least 70% compared to the concentration found in infants not fed prebiotics or resulting in a faecal proportion of less than 1.5% of total SCFA. The proportion of branched SCFA relative to the total SCFA can be measured by dividing the sum of branched SCFAs, i.e. isobutyrate, plus isovalerate plus valerate, by the sum of total SCFA, i.e. acetate, plus propionate, plus butyrate, plus isobutyrate, plus isovalerate, plus valerate, etc.

Reducing the proportion of branched SCFA is beneficial to the health of the subject, as branches SCFA are damaging. This indicates less protein degradation, which is unwanted because protein fermentation results in an increase of pH and in the formation of damaging agents such as $H_2S$.

A significant decrease of butyrate relates to a decrease by at least 50% compared to the concentration found in infants not fed prebiotics or resulting in a faecal proportion of less than 4% of total SCFA. In one embodiment the composition according to the invention is suitable for decreasing the sum of intestinal (and/or faecal) butyrate, isobutyrate, valerate and isovalerate is below 7% of total SCFA, such as 6.5%, 6%, 5%, 4% or less of total SCFA.

In another embodiment, compositions comprising GOS and polyfructose are suitable to increase the length of fermentation within the colon. In particular, bacterial fermentation will still be active in the most distal parts of the colon following co-administration, as indicated by SCFA production in the distal part of the colon. No or only very little SCFA is produced in the distal part of the colon following administration of compositions comprising only GOS or only polyfructose. In addition, fast fermentation at the beginning of the colon is seen following co-administration, which is especially important for anti-pathogenic effects and is also observed in breast fed infants. Overall, this indicates the compositions are suitable for establishing and/or maintaining a relatively even fermentation pattern throughout the colon of a subject and to extend fermentation and SCFA production to the distal end of the colon. SCFA, and most likely also other fermentation products, especially lactate, are therefore produced throughout the colon, in the beginning, middle and end of the colon.

In a further embodiment, co-administration of GOS and polyfructose in synergistic amounts may be used for significantly increasing lactate production, as can be determined again by analysing faecal samples of test subjects and control subjects, which received compositions comprising either GOS alone or polyfructose alone or equivalent base compositions without prebiotics. A "significant increase in lactate" refers to at least 5%, 10%, 20% or even 50% or more lactate being produced in subjects being co-administered compositions comprising GOS and polyfructose, compared to subjects not administered GOS or polyfructose. For example, infants fed on standard milk formula supplemented with 6 g/l of TOS/inulin mixtures (90%:10%) produced at 16 weeks about 16% lactate (as % of total acids), while standard formula fed infants produced about 0.6% and breast fed infants produced about 35% lactate. Although not matching the amount of lactate produced by breast fed infants, the supplementation of the standard milk formula with TOS and inulin mixtures led to a significant increase in lactate production. As shown in the Examples, lactate was found to have unexpected beneficial effects. Similarly to acetate it increased the prostaglandin E1 and prostaglandin E2 production and resulted in enhanced epithelial mucin expression. The intestinal mucosa plays an important role in human health, as it serves as a barrier to infectious pathogens, allergens and carcinogens. Compositions which positively influence the development and/or integrity of the mucosa may therefore be used to aid the build up of a healthy mucosa in new born infants and to aid the establishment of a healthy mucosa in bottle-fed or partially bottle-fed infants and in subjects suffering from symptoms or diseases resulting from or being associated with a not properly functioning intestinal mucosa. For example, intestinal problems, such as Inflammatory Bowel Disease (IBD, for example colitis or Crohn's disease) or Irritable Bowel Syndrome (IBS) may be treated or prevented, or pathogen attachment and/or entry through the mucosa may be reduced or other immunological problems, such as the development of asthma, may be prevented or reduced. Also the loss of intestinal barrier integrity as a result from malnutrition, surgery, chemotherapy etc. can be prevented or reduced.

Furthermore, spontaneous contractions and abdominal tension was significantly reduced in a dose dependent manner following D- or L-lactate administration. The compositions according to the invention may thus be used to increase intestinal lactate levels and thereby treat or prevent symptoms such as abdominal pain, colic, abdominal contractions, abdominal tension and the like.

As lactate itself was found to have previously unknown effects, it is also an object of the invention to provide compositions comprising lactate in suitable amounts, which may be used to treat or prevent the above described symptoms and disorders. In one embodiment compositions comprises only lactate in suitable amounts, while in another embodiment the GOS an polyfructose compositions described herein further comprises lactate to further increase intestinal lactate levels. One such composition according to the invention comprises TOS and inulin in synergistically effective amounts and further comprises lactate in suitable amounts. In one embodiment compositions are provided which are suitable for increasing intestinal and/or faecal lactate to above about 10 mmol/kg faeces.

It is understood that when referring to the analysis of faecal samples this is an indirect measure of the actual in vivo effect. Likewise, in vitro assays may be carried out, whereby bacterial populations are grown in vitro and suitable amounts of compositions are added to the cultures. In particular, the in vitro fermentation system described in the Examples may be used.

Co-administration of compositions comprising GOS and polyfructose can therefore be used to achieve one or more of the following physiological effects:
  a significant increase in total SCFA
  a significant decrease in pH
  a significantly modified SCFA composition
  a significant decrease in branched SCFA
  a significant decrease in gas production per mol SCFA produced
  a longer and more even fermentation, including fermentation even in the most distal parts of the colon, and/or
  a high initial formation of SCFA and/or lactic acid formation in the most proximal part of the colon
  promoting the production of SCFA at the beginning, middle and end of the colon
  a significant increase in lactic acid (absolute and/or relative) and/or
  an increase in the relative amount of L-lactate as a ratio of total lactic acid formed.

In a preferred embodiment at least 2, 3, 4, 5, 6, 7, 8, 9 or all these effects are significantly modified when using compositions comprising both GOS and polyfructose, compared to when administering compositions comprising only GOS or polyfructose, or neither GOS or polyfructose. In particular, at least 2, 3, 4, 5, 6, 7, 8, 9 or all these effects are significantly larger following co-administration of a (synergistically effective amount) of GOS and polyfructose than the sum of the effect(s) of administration of GOS and polyfructose individually.

The synergistic compositions according to the invention are, therefore, particularly suited to build up and/or maintain a healthy microflora within an infant's large intestine following administration of a synergistically effective amount. In a preferred embodiment an infant is fed solely on a base composition, such as milk formula, supplemented with a synergistically effective amount of GOS and polyfructose within the first weeks after birth. A preferred composition is, therefore, a dietary composition for infants. In another embodiment an infant is only partly fed on a composition according to the invention. In one embodiment the composition is used to treat or prevent symptoms selected from one or more of: gas formation, flatulence, colitis, abdominal bloating, abdominal cramps, abdominal pain, IBS, IBD, allergy and/or as a mucoprotectant. GOS and polyfructose may, thus, be used for the preparation of a composition or a combined composition for simultaneous, separate or sequential use in treatment of flatulence, excessive gas formation, colitis, abdominal bloating, abdominal cramps, abdominal pain, IBS, IBD, allergy, decreased intestinal barrier functioning and/or as a mucoprotectant. The subject may in this case be any subject, ranging from infant, child, teenager to adult. Clearly, the base compositions to which GOS and polyfructose are added in synergistically effective amounts, will vary depending on the age of the subject, the mode of administration and on the main symptoms to be treated or prevented. For infants for example the base composition is preferably a liquid or powder form infant or follow-on formula, while for adults a nutrient supplement composition (liquid, semi-liquid or solid) or tube feeding may be more suitable.

In a preferred embodiment GOS and polyfructose are co-administered in a synergistically effective amount suitable to significantly increase the total amount of intestinal SCFA formed and/or to significantly improve intestinal SCFA composition (especially to significantly increase the percentage of acetate relative to the total amount of SCFA)

and/or to significantly increase lactate production and/or to and to lower intestinal pH and/or to significantly reduce intestinal gas formation.

Use of compositions comprising a synergistically effective amount of GOS and polyfructose for the treatment and/or prevention of colic and/or abdominal cramps, abdominal bloating and/or flatulence, abdominal pain, IBS, IBD and/or allergy is provided. Use of such compositions for increasing mucoprotection and strengthening the intestinal barrier is also provided. It is understood that not necessarily one composition is referred to, but that GOS and polyfructose may be present in separate compositions, which provides a synergistically effective amount when co-administered.

Through these changes in SCFA levels, profile and intestinal pH, the compositions are able to cause one or more of the following downstream beneficial effects:

a) The intestinal permeability at the site of SCFA production is decreased. This is important for preventing disease and maintaining health, especially to prevent allergies from developing. The finding that co-administration of GOS and polyfructose causes more even fermentation and extends fermentation to the distal part of the colon is important in this respect, as the permeability of the intestine, including the distal parts of the colon, can be evenly reduced and the intestine can thereby be evenly maintained in a healthy state.

b) The motility or peristaltic movement of the intestine is enhanced, which reduces or prevents constipation, a common problem observed in formula fed infants.

c) Decreasing the amount of spontaneous contractions and the colonic muscle tension resulting in less cramps and less abdominal pain.

d) Calcium-ion absorption is increased, which is important for bone mineralisation and bone development of the subject, especially if the subject is an infant e) Secondary symptoms of reduced health such as fatigue, depression and mood fluctuation may be reduced, f) Mucus production of the intestinal mucosa is significantly enhanced, which provides protection against pathogen attachment and colonization. In particular, it was found that lactate levels correlated positively with mucus production. The compositions according to the invention may thus be used to stimulate mucus production.

g) Bile metabolism may be modified to levels and/or patterns as observed in breast fed infants.

h) Growth of intestinal pathogenic microorganisms is inhibited along the entire colon.

A composition comprising a synergistically effective amount of GOS and polyfructose may therefore be used to either maintain or establish (e.g. in a newborn, premature or mature born baby or in a non- or partially breast fed baby, or other subjects, such as adults, one or more of the above physiological effects and maintain or improve the health of the subject by ensuring or establishing a healthy large intestinal environment and optimal activity of the large intestine.

In particular, incidence, duration and/or severity of diseases, disorders or symptoms such as colic and/or abdominal cramps, abdominal bloating and/or flatulence, abdominal pain, IBS, IBD and/or allergy, intestinal pathogen infection (e.g. bacteria, viruses, fungi), diarrhoea, eczema, allergy induced asthma and other atopic diseases, and/or constipation can be reduced, abolished or prevented by administration of a composition according to the invention. The compositions according to the invention may also be used to relax contractions of the colon, preferably the phasic and/or tonic contractions.

Compositions According to the Invention

Compositions suitable for the uses described above comprise both polyfructose and GOS in synergistically effective amounts. The compositions comprise GOS/polyfructose in ratios ranging from 3/97 to 97/3, preferably 5/95 to 95/5, more preferably 90/10 to 45/55. All individual ratios between these end-points are encompassed herein, such as 10/90, 20/80, 30/70, 40/60, 50/50, 55/45, 60/40, 70/30, 80/20, 85/15, 90/10, etc.

The dosages required and the GOS/polyfructose ratio for achieving the (optimal) synergistic effect may vary, depending on the type of composition and the method and frequency of administration. A few examples are however given below. A skilled person may easily determine what dosages of each component is required to achieve the best physiological effect and what GOS/polyfructose ratio is the most suitable. For example, if the main aim is to enhance the total level of SCFA following oral administration of a composition comprising GOS and polyfructose, a skilled person will make various compositions (comprising GOS plus polyfructose, GOS alone, polyfructose alone) and compare their efficiency in inducing high SCFA levels using either in vivo or in vitro tests as known in the art. It is understood that when referring to "daily dose" or 'dosage per day', this does not imply that the dosage must be administered to the subject at one time.

A synergistically effective infant formula may, for example, consist of a base composition (e.g. standard infant formula) comprising about 4 g/l, 5 g/l or more of a mixture of GOS and polyfructose, whereby the ratio's of GOS to polyfructose may vary as described elsewhere herein (e.g. 90% GOS:10% polyfructose).

Polyfructose may, for example, be levan and/or inulin. Polyfructose, such as levan or inulin, for use in the compositions may be either extracted from natural sources (plants or bacteria) or may be made by de novo synthesis or by recombinant DNA technologies as known in the art. Extraction, size separation and purification methods of inulin have been described, for example in De Leenheer (1996), U.S. Pat. Nos. 6,569,488 and 5,968,365. Recombinant production methods have been for example described in U.S. Pat. No. 6,559,356. Synthesis generally involves the use of sucrose molecules and enzymes with fructosyl transferase activity. Inulin suitable for use in the compositions is also already commercially available, e.g. Raftiline®HP, Orafti.

Plant inulins generally have a much lower degree of polymerisation than bacterial inulins (up to 150, compared to up to 100,000 in bacteria). Plant sources include dicotyledenous species, such as Compositae. Examples of species which produce relatively large amounts of inulin, mainly in their roots, bulbs or tubers, are chicory, asparagus, dahlia, Jerusalem artichoke, garlic, and others (see Kaur and Gupta, J. Biosci. 2002, 27, 703-714). As the inulin should preferably not comprise oligofructose, hydrolysis should be avoided or oligofructose and/or mono- or disaccharides present should be removed prior to use.

Especially preferred is polyfructose with a PD of at least 10, 15, 20, 50, 70, 100, 120, 130, 150, 200, 300, 500 or more. Polyfructoses, such as levans, may be hydrolysed to avoid viscosity problems associated with too long chains, as long as a PD of 10 or more is retained.

Levans may also be obtained from natural sources such as plants (e.g. monocotyledons) yeast, fungi, bacteria, or made chemically or using recombinant DNA technology.

GOS may be obtained from natural sources, such as plants (e.g. chicory, Soya) or bacteria, or may be made synthetically or by recombinant DNA technology as known in the art. GOS may be β-galacto-oligosaccharide or α-galacto-oligosaccharide or a mixture of both. In particular, galactose residues are linked by β(1-4) and β(1-6) glycosidic bonds (trans GOS or TOS). GOS suitable for use in the compositions is also already commercially available, e.g. Vivinal®GOS, Borculo Domo Ingredients, Zwolle, The Netherlands. GOS may also be derived from lactose, by treatment of lactose enzymatically with β-galactosidase or by hydrolysis from polyglucan. In a preferred embodiment TOS is used. In one embodiment the preferred polyfructose is inulin HP, so that the combination of TOS and inulin HP are also a preferred embodiment herein.

Other compositions provided are compositions comprising lactate in suitable amounts, in particular for the uses described above. Suitable amounts of lactate may vary, and may for example range from 1 to 30 grams per day.

Compositions according to the invention may be either food compositions, food supplement compositions or pharmaceutical compositions. Apart from polyfructose and GOS (and/or lactate) they may comprise additional ingredients. For food compositions or food supplement compositions these should be food grade and physiologically acceptable. "Food" refers to liquid, solid or semi-solid dietetic compositions, especially total food compositions (food-replacement), which do not require additional nutrient intake or food supplement compositions. Food supplement compositions do not completely replace nutrient intake by other means. Food and food supplement compositions are in a preferred embodiment baby food or food supplements, food or food supplements for prematurely born babies, infant food, toddler food, etc., which are preferably administered enterally, preferably orally several times daily. The food or food supplement compositions are particularly suited for non- or partially breast fed infants. Also, the composition may be beneficially administered to infants in their adaptation period to solid food or infants changing from breast to bottle feeding. The composition may also be part of a human milk fortifier supplement.

In one embodiment the composition is an infant or follow-on formula as e.g. known in the art, especially as described in the European Commission directive 91/321/EEC and the amendments thereof, but may be modified to comprise an effective amount of polyfructose and GOS. The infant or follow-on formula may be based on milk (cows milk, goats milk, etc.), infant milk formula (IMF) or soy for lactose intolerant infants or may contain amino acids as a nitrogen source for infants having problems regarding allergy or absorption. Commercially available infant or follow-on formulae comprise, thus, a milk protein or soy protein base, fat, vitamins, digestible carbohydrates and minerals in recommended daily amounts and may be powders, liquid concentrates or ready-to-feed compositions.

Administration of the modified infant or follow-on formula results in a large intestinal environment which resembles that of breast-fed infants, as can be determined by analyses of faecal pH, bacterial composition, SCFA production and profiles, gas production, etc. When the composition is a drink, preferably the volume (comprising the daily effective dose) consumed or administered on a daily basis is in the range of about 100 to 1500 ml, more preferably about 450 to 1000 ml per day. When the formula is a solid preferably the amount (comprising the daily effective dose) consumed or administered on a daily basis is in the range of about 15 to 220 g/day, preferably about 70 to 150 g/day of formula powder.

A daily effective dose of GOS and polyfructose ranges from about 1 to 30 g/day, preferably from about 2 to 10 g/day for infants and preferably for adults from about 5 to 20 g/day.

Food or food supplement compositions according to the invention may additionally comprise other active ingredients, such as vitamins (A, B1, B2, B3, B5, B12, C, D, E, K, etc.), probiotics (e.g. bifidobacteria, lactobacilli, etc.), other prebiotics, fibres, lactoferrin, immunoglobulins, nucleotides, and the like. Nutrients such as proteins, lipids and other carbohydrates (e.g. digestible carbohydrates, non-digestible carbohydrates, soluble or insoluble carbohydrates) may be present in various amounts. Typical in-soluble non-digestible carbohydrates present in infant nutrition are soy polysaccharides, resistant starch, cellulose and hemicellulose. Typical soluble and digestible carbohydrates for use in infant nutrition are for example maltodextrin, lactose, maltose, glucose, fructose, sucrose and other mono- or disaccharides or mixtures thereof. The composition may also comprise other inactive ingredients and carriers, such as e.g. glucose, lactose, sucrose, mannitol, starch, cellulose or cellulose derivatives, magnesium stearate, stearic acid, sodium saccharin, talcum, magnesium carbonate and the like. The compositions may also comprise water, electrolytes, essential and non-essential amino acids, trace elements, minerals, fibre, sweeteners, flavorings, colorants, emulsifiers and stabilisers (such as soy lecithin, citric acid, esters of mono- or di-glycerides), preservatives, binders, fragrances, and the like.

Lipids suitable for the compositions, especially for infant food or food supplements, are milk fats, plant lipids, such as canola oil, safflower oil, sunflower oil, olive oil, marine oils, etc. or fractions or mixtures thereof comprising suitable fatty acids (polyunsaturated and/or saturated).

Proteins suitable for the compositions especially for infant food or food supplements, include casein, whey, condensed skimmed milk, soy, beef, collagen, corn and other plant proteins or hydrolysed proteins, free amino acids, etc. Preferably proteins comprised in infant food or food supplement compositions are extensively hydrolysed and/or partially hydrolysed to reduce the risk of allergies. The infant food compositions according to the invention preferably comprise all vitamins and minerals essential in the daily or weekly diet in nutritionally significant amounts, such as minimal recommended daily amounts.

The food or food supplement composition may also in one embodiment be made on the basis of (i.e. starting from or comprising) a food base. It may, for example, based on, or comprises, a dairy product, such as a fermented dairy product, including but not limited to milk, yoghurt, a yoghurt-based drink or buttermilk. Such compositions may be prepared in a manner known per se, e.g. by adding an effective amount of polyfructose and GOS or TOS to a suitable food or food base. Other food bases suitable may be plant bases, meat bases and the like.

The food or food supplement composition according to the invention may be used either as a treatment and/or prophylactically. This is to say that they may be either administered after gastrointestinal problems or diseases have been diagnosed in a subject or, alternatively, prior to the occurrence of symptoms (for example to high risk patients, likely to develop gastrointestinal problems). For example, if symptoms associated with the disease or suboptimal functioning if the large intestine, such as constipation, flatulence, allergies, colics, abdominal pain, abdominal cramps, IBD, IBS are observed, administration of the composition will aid in re-establishing a healthy large intestinal environment or prevent the development of such symptoms.

In one embodiment the compositions are administered prophylactically, to support the development of a healthy microflora and/or healthy large intestinal environment. A "healthy large intestinal environment" refers to a normal intestinal physiology and activity, especially normal absorption of nutrient, water, resistance of the mucosa to pathogen attachment, colonisation and infection, etc. as can be determined by faecal analysis and gas production. Especially, an optimal physiology and activity is referred to. Any suboptimal functioning of the large intestine results in symptoms as described and can be determined by faecal analysis and/or gas production. Intestinal diseases or disorders resulting from a suboptimal functioning are included herein.

Pharmaceutical compositions for the treatment or prophylaxis of intestinal disorders or symptoms of suboptimal intestinal functioning, such as IBD, colitis, IBS and/or increased barrier integrity may comprise additional biologically active ingredients, such as drugs, biologically active proteins or peptides, probiotics, and others. The embodiments described for food or food supplement compositions apply also to pharmaceutical compositions.

The compositions according to the invention may be in any dosage form, such as liquid, solid, semi-solid, tablets, drinks, powders, etc., depending on the method of administration. Administration to a subject is preferably oral, although for some uses rectal or tube feeding (with a tube directly entering the stomach, duodenum, or small intestine or large intestine) may be suitable.

It is a further embodiment of the invention to provide a method for the manufacture of a composition according to the invention by adding a synergistically effective amount of GOS (or TOS) and polyfructose to a suitable composition base, as described above.

The following non-limiting Examples describe the synergistic effect of GOS and polyfructose. Unless stated otherwise, the practice of the invention will employ standard conventional methods of molecular biology, pharmacology, immunology, virology, microbiology or biochemistry. Such techniques are described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and Remington's Pharmaceutical Sciences, Mack Publishing Company, Philadelphia, Pa., 17th ed. (1985), *Microbiology: A Laboratory Manual* (6th Edition) by James Cappuccino, *Laboratory Methods in Food Microbiology* ($3^{rd}$ edition) by W. Harrigan (Author) Academic Press, all incorporated herein by reference.

Formation of acetate, propionate and butyrate after 48 h in vitro fermentation of TOS, Inulin, a mixture of TOS/Inulin 9/1 and a mixture of oligofructose and inulin 1/1 by fresh faeces obtained from babies.

FIG. 2

Relative amounts of acetate, propionate and butyrate formed after 48 h in vitro fermentation of TOS, Inulin, a mixture of TOS/Inulin 9/1 and a mixture of oligofructose and inulin 1/1 by fresh faeces obtained from babies. The sum of acetate plus propionate plus butyrate formed was set at 100% for each of the fibre tested.

FIG. 3

Formation of gas after 48 h in vitro fermentation of TOS, Inulin, a mixture of TOS/Inulin 9/1 and a mixture of oligofructose and inulin 1/1 by fresh faeces obtained from babies. The amount of gas formed (ml was related to the amount of total SCFA formed (in mmol per g fibre)

Figure 4A:
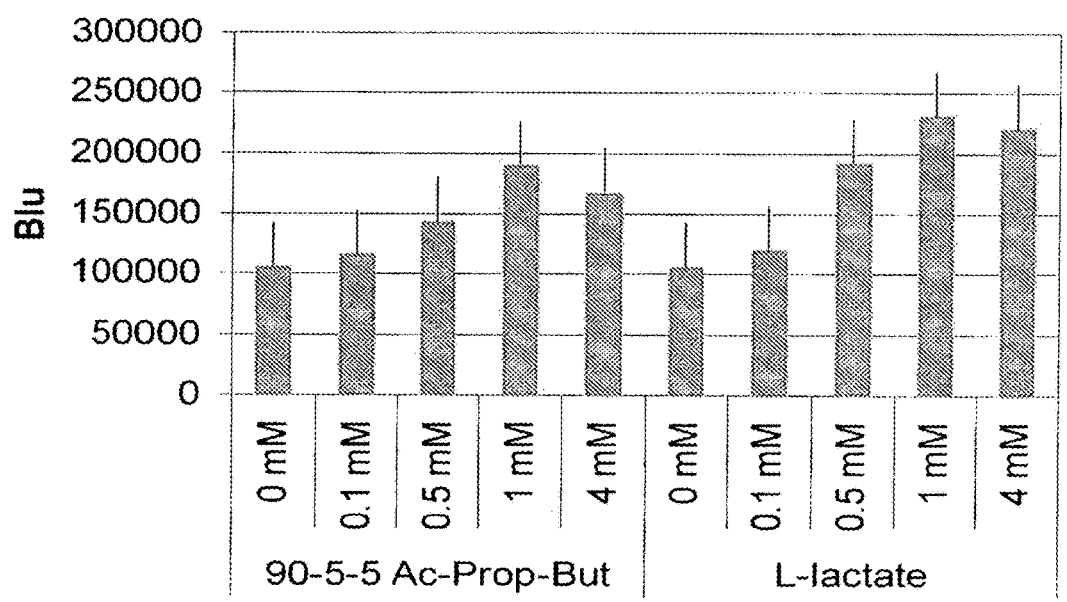
Figure 4B:
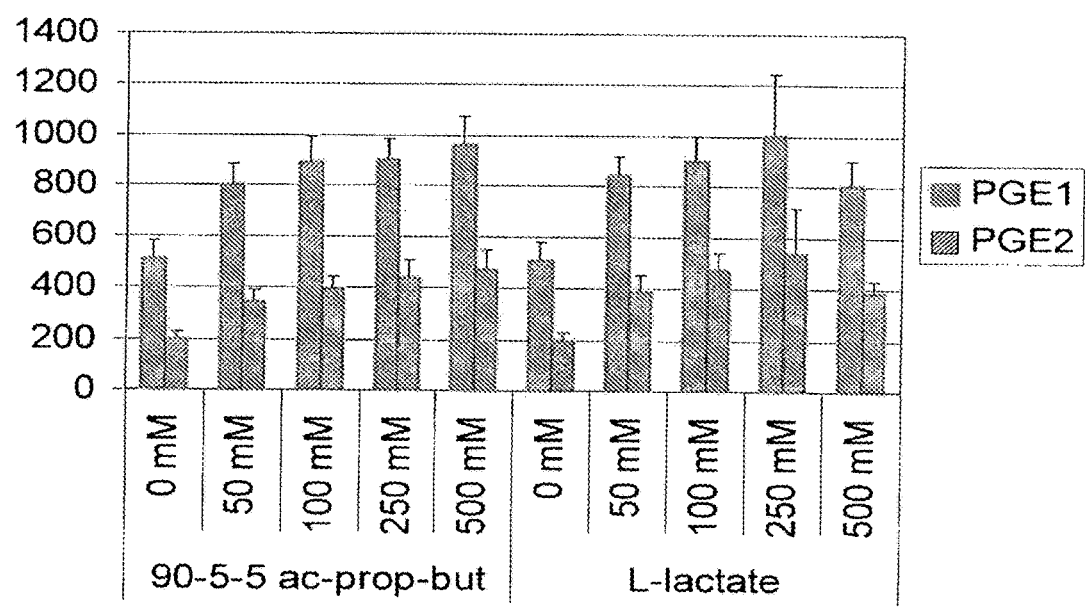

FIGS. 4a and 4b

Effects of Mixtures of SCFA (Acteate/Propionate/Butyrate in a Ratio of 90/5/5 on a Molar Basis) and of L-Lactate.

FIG. 4a: Effect of 0, 0.1, 0.5, 1 and 4 mM of the SCFA mixture or L-lactate on muc-2 expression in a CCD18/T84 co-culture (n=6). Error bars show the SEM. The increase at 1 and 4 mM SCFA mixture and 0.5, 1 and 4 mM L-lactate is statistically significant.

FIG. 4b: Effect of 0, 50, 100, 250 and 500 µM SCFA mixture or L-lactate on the spontaneous PGE1 and PGE2 response in CCD18 cells (n=7). Error bars show the SEM. The increase of PGE1 at 100, 250 and 500 µM SCFA mixture and 100 µML-lactate is statistically significant. The increase of PGE2 at 100, 250 and 500 µM SCFA mixture and 250 µM L-lactate is statistically significant (P<0.05)

FIG. 5

Effects of sodium acetate and sodium L-lactate on the spontaneous contraction in the distal and proximal part of the colon. The blanc (set to a tension of 1 g) is 0%. The tension after addition of 40 mM KCl was set to 100%.

EXAMPLES

Example 1

In Vitro Fermentation Studies Show Synergistic Effects on Fermentation Patterns 1.1 Materials and Methods Microorganisms Microorganisms were obtained from fresh faeces from bottle fed babies. Fresh faecal material from babies ranging 1 to 4 month of age was pooled and put into preservative medium within 2 h.

Compositions/Substrate

As substrate either prebiotics (TOS; TOS (from Vivinal-GOS, Borculo Domo Ingredients, The Netherlands) and inulin (raftilinHP from Orafti, Belgium) mixture in a 9/1 (w/w) ratio; inulin; oligofructose and inulin mixture in a 1/1 (w/w) ratio, or none (blanc) was used.

Media

McBain & MacFarlane medium: Buffered peptone water 3.0 g/l, yeast extract 2.5 g/l. mucin (brush borders) 0.8 g/l, tryptone 3.0 g/l, L-Cysteine-HCl 0.4 g/l, bile salts 0.05 g/l, $K_2HPO_4.3H_2O$ 2.6 g/l, $NaHCO_3$ 0.2 g/l, NaCl 4.5 g/l, $MgSO_4.7H_2O$ 0.5 g/l, $CaCl_2$ 0.228 g/l, $FeSO_4.7H_2O$ 0.005 g/l. 500 ml Scott bottles were filled with the medium and sterilised for 15 minutes at 121° C.

Buffered medium: $K_2HPO_4.3H_2O$ 2.6 g/l, $NaHCO_3$ 0.2 g/l, NaCl 4.5 g/l, $MgSO_4.7H_2O$, 0.5 g/l, $CaCl_2$ 0.228 g/l, $FeSO_4.7H_2O$ 0.005 g/l. pH was adjusted to 6.3±0.1 with $K_2HPO_4$ or $NaHCO_3$. 500 ml Scott bottles were filled with the medium and sterilised for 15 minutes at 121° C.

Preservative medium: Buffered peptone 20.0 g/l, L-Cysteine-HCl 0.5 g/l, Sodium thioglycollate 0.5 g/l, resazurine tablet 1 per liter. pH was adjusted to 6.7±0.1 with 1 M NaOH or HCl. The medium was boiled in microwave. 30 ml serum bottles were filled with 25 ml medium and sterilised for 15 minutes at 121° C.

The fresh faeces were mixed with the preservative medium. Fresh faeces can be preserved in this form for several hours at 4° C.

Faecal suspension: The preserved solution of faeces was centrifuged at 13,000 rpm for 15 minutes. The supernatant was removed and the faeces was mixed with the McBain & Mac Farlane medium in a weight ratio of 1:5.

Fermentation 3.0 ml of the faecal suspension were combined with 85 mg glucose or prebiotic or with no addition (blanc) in a bottle and mix thoroughly. A t=0 sample was withdrawn (0.5 ml). 2.5 ml of the resulting suspension was brought in a dialysis tube in a 60 ml bottle filled with 60 ml of the buffered medium. The bottle was closed well and incubated at 37° C. Samples were taken from the dialysis tube (0.2 ml) or from the dialysis buffer (1.0 ml) with a hypodermic syringe after 3, 24, and 48 hours and immediately put it on ice to stop fermentation.

Determination of the Short Chain Fatty Acids and Lactate

See Example 2. Values were corrected for blanc.

Gas Determination

At t=3, t=24 and t=48 the gas pressure in the head space of the 60 ml bottle was measured by a gas pressure meter (Druckmessumformer, Econtronic, Germany) by stinging a hypodermic 6 ml syringe through the rubber cap of the bottle and withdrawal of gas from the headspace by this syringe until the gas pressure was 0 bar. The volume in the syringe was the volume of gas formed. Values were corrected for blanc.

1.2 Results

In vitro fermentation was carried out using the following samples:
1.) 85 mg TOS (from VivinalGOS, Borculo Domo Ingredients, The Netherlands)
2.) 85 mg inulin (RaftilinHP, from Orafti, Belgium)
3.) 85 mg TOS/inulin with a ratio of TOS/inulin of 9/1 (w/w) and
4.) 85 mg OF (raftiloseP95, from Orafti, Belgium)/inulin (raftilinHP) in a ratio of OF/inulin of 1/1 (w/w).

Total Amount of SCFA Produced

Figure 1:
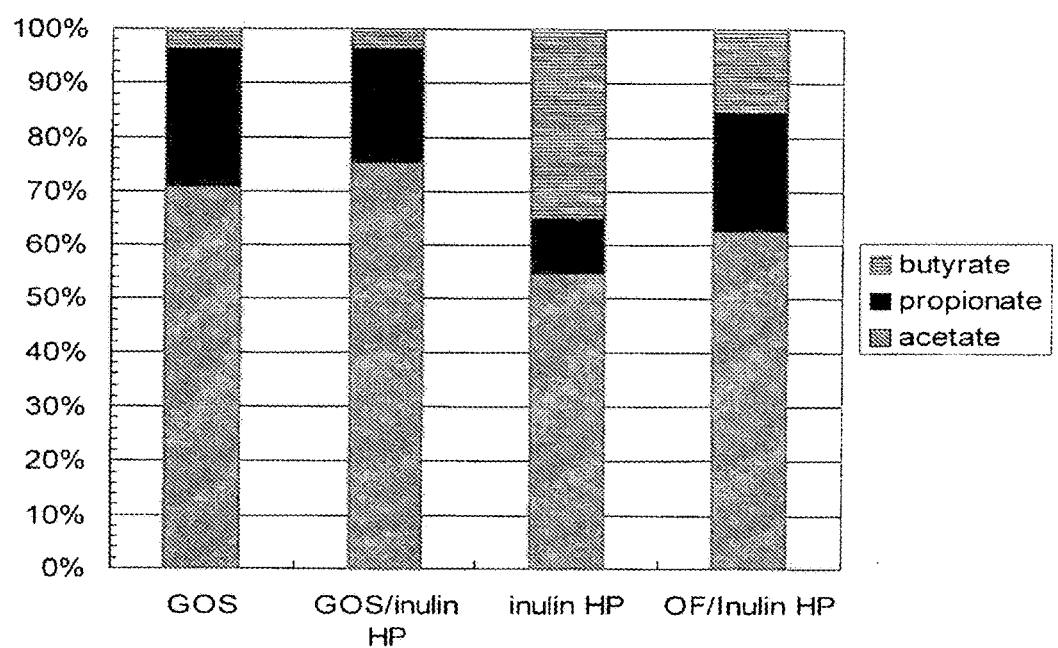
FIG. 1

Results are shown in FIG. 1. FIG. 1 shows that the mixture of TOS/Inulin resulted in a significantly higher amount of SCFA per g fibre than the single components, but also higher than the mixture of oligofructose (OF) and inulin. Also tested were 85 mg TOS/inuline in a ratio of 1/1 (data not shown), which also provided a synergistic effect.

L- and D-Lactate Production

L- and D-lactate could only be determined at t=3. Table 1 shows the metabolic end products formed at that time point.

TABLE 1 metabolic end-products (mmol/g fibre) formed after 3 hours in vitro fermentation

|  | Acetate | Propionate | Butyrate | L-lactate | D-lactate |
| --- | --- | --- | --- | --- | --- |
| TOS | 0.23 | 0 | 0 | 0.14 | 0.03 |
| Inulin | 0 | 0 | 0 | 0.00 | 0.00 |
| TOS/Inulin | 0.40 | 0 | 0 | 0.17 | 0.04 |
| OF/Inulin | 0.30 | 0 | 0 | 0.04 | 0.02 |

Again a synergistic higher formation of lactate is observed for the mixture TOS/Inulin compared to the single components TOS and Inulin. Compared to the mixture with OF and Inulin the percentage lactate (based on total acids) and ratio L-/D-lactate is higher in the TOS/Inulin mixture.

Relative Amounts of SCFA

Figure 2:
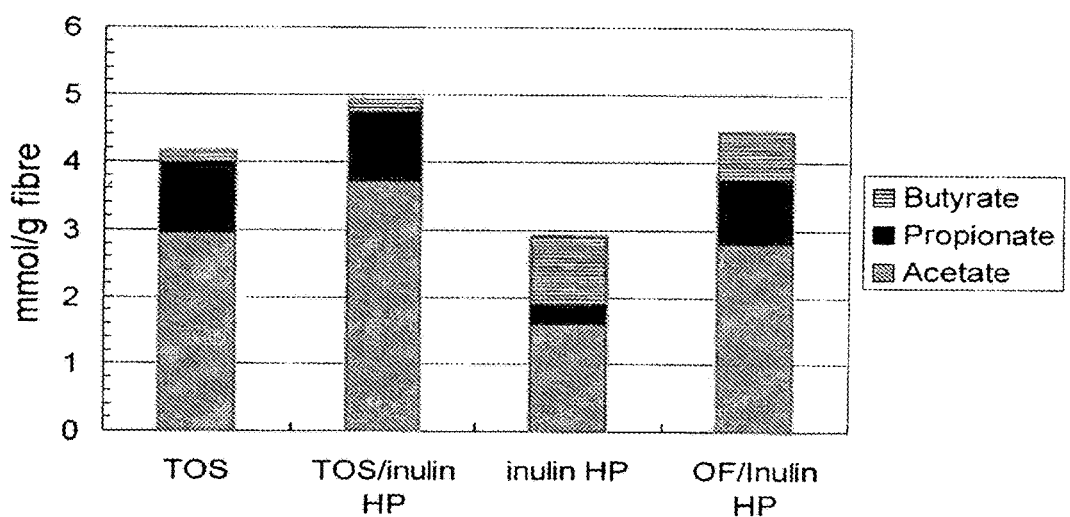

FIG. 2 shows the pattern of fermentation products after 48 h. The mixture of TOS/inulin shows a significantly higher percentage of acetate than the single components, which is also higher than for the mixture of oligofructose (OF) and Inulin. Faeces of breast fed babies show a high percentage of acetate, so the mixture of TOS/Inulin results in a pattern of fermentation products which most resembles that of breast fed babies.

Gas Formation

Results are shown in FIG. 3. Regarding the formation of gas, TOS and the mixture TOS/Inulin form the lowest amount of gas per mmol SCFA formed. Inulin and the mixture of OF/inulin show a much higher amount of gas formation. Per mmol SCFA formed the amount of gas is lowest in the TOS/inulin mixture.

Kinetics of SCFA Formation

Table 2 shows the kinetics of SCFA formation. The combination of TOS/inulin still shows a high SCFA formation between 24 and 48 h, indicating that in the distal part of the colon still SCFA is formed and having a beneficial effect on the colon permeability, mucus formation and anti-pathogenic effects etc. Also in the first 3 h the highest amount of SCFA is formed, as is the case with human milk oligosaccharides (data not shown). A fast fermentation at the beginning of the colon is of importance because of the antipathogenic effects.

TABLE 2 kinetics of SCFA formation (mmol) SCFA (blanc corrected)

|  | Time interval (hours) | | |
| --- | --- | --- | --- |
| Prebiotics | 0-3 hrs | 3-24 hrs | 24-48 hrs |
| TOS | 0.23 | 3.85 | 0.13 |
| TOS/inulin HP | 0.40 | 4.49 | 0.24 |
| Inulin HP | 0.00 | 3.05 | 0.05 |
| OF/Inulin HP | 0.11 | 4.26 | 0.00 |

OF = oligofructose

Example 2

Clinical study with TOS/Inulin: A relative increase of acetate and relative decrease of butyrate is not correlated with an increase of Bifidobacteria. TOS and Inulin have a synergistic effect.

2.1 Materials and Methods 63 pregnant woman who had decided to breast-feed and 57 who chose not to, were recruited during their last trimester of pregnancy. Infants with normal birth weight, no congenital abnormality, congenital disease or gastrointestinal disease were enrolled within 3 days after delivery. The study was approved by the ethical committee of the Medical Center, St. Radboud, Nijmegen, The Netherlands. Written informed consent was obtained from the parents before enrolment in the study.

Infants of mothers who had decided not to breast-feed, were randomly and double blindly allocated to one of two formula groups (OSF, SF). The standard formula group (SF; n=19 received a regular, non-supplemented infant formula (Nutrilon I, Nutricia, The Netherlands). The main compositional data of the standard formula at standard dilution of 131 g/l are given in Table 3. The prebiotic formula group (OSF; n=19) received the same standard infant formula supplemented with a mixture of 6 g/l transgalacto-oligosaccharides (TOS; Vivinal GOS, Borculo Domo Ingredients, Zwolle, The Netherlands) and inulin (PF; RaftilineHP, Orafti active food ingredient, Tienen, Belgium). The mixture comprised 90% TOS and 10% inulin (polyfructose). The study formulas were fed ad libitum during the study period.

Mothers who decided to breast feed were stimulated to continue breast feeding during the course of the study and were supported by a lactation consultant when needed. At termination of breast feeding their infants received one of two formulae. Compliance was assessed by counting the number of unused formula tins during each visit and comparing the amount of consumed formula with the recorded food intake.

TABLE 3

Composition of the standard formula per litre

| | | |
|---|---|---|
| Energy | kcal | 670 |
| Protein | g | 14 |
| Casein/whey ratio | | 40/60 |
| Fat | g | 35 |
| Total carbohydrates | g | 75 |
| Lactose | g | 75 |
| Minerals | | |
| Calcium | mg | 540 |
| Phosphorus | mg | 270 |
| Magnesium | mg | 50 |
| Sodium | mg | 190 |
| Potassium | mg | 680 |
| Chloride | mg | 430 |
| Iron | mg | 5 |
| Zinc | mg | 5 |

Questionnaires

Demographic, clinical and anthropometrical data of the mother are collected prior to delivery. Information on delivery was obtained from the mothers at day 5 after delivery. Information of the infants' food intake, formula tolerance, stool characteristics, health and anthropometrics was obtained from questionnaires at postnatal day 5, 10, 28 and once every 4 weeks thereafter until the end of the study.

Faecal Samples

Parents were asked to take faecal samples from their infants, at postnatal day 5, 10, 28 and once every 4 weeks thereafter. The samples were taken from the diaper, as soon as possible after defecation, collected in faeces containers (Greiner Labortechnik, the Netherlands) and stored immediately at −20° C. by the parent and transported in a portable freezer to the laboratory by the investigators.

Preparation of Faecal Samples:

For the determination of SCFA, 1 gram of the samples was thawed in ice water diluted 10× in MilliQ and homogenised for 10 minutes using a stomacher (IUL Instruments, Barcelona, Spain). 350 µl homogenised faeces was mixed with 200 µl 5% (v/v) formic acid, 100 µl 1.25 g/l 2-ethylbutyric acid (Sigma-Aldrich, Zwijndrecht, The Netherlands) and 350 µl MilliQ. The samples were centrifuged for 5 minutes at 14,000 rpm to remove large particles and the supernatant was stored at −20° C. For the FISH analysis and lactic acid measurements, the samples were thawed in ice water, diluted 10× (w/v) in phosphate buffered saline, pH 7.4 (PBS) and homogenized for 10 minutes using a stomacher. The homogenised faeces were stored at −20° C.

Fluorescence In Situ Hybridisation

FISH analysis was performed as described (Langendijk et al, 1995, Appl. Environ. Microbiol. 61:3069-3075.) with some slight modifications. Paraformaldehyde fixed samples were applied to gelatin coated glass slides (PTFE coated 8-wells [1 cm2/well] object slides, CBN labsuppliers, Drachten, The Netherlands) and air-dried. The dried samples were dehydrated in 96% ethanol for 10 minutes. Hybridisation buffer (20 mm Tris-HCl, 0.9 M NaCl, 0.1% SDS [pH 7.1[) with 10 ng/l Cy3 Labeled *Bifidobacterium* specific probe Bif164mod (5'-CAT CCG GYA TTA CCA CCC), was preheated and added to the dried samples. Bif 164 mod is modified version of probe S-G-Bif-a-0164-a-A-18 ((Langendijk et al, 1995, Appl. Environ. Microbiol. 61:3069-3075.). The slides were incubated overnight in a dark moist chamber at 50° C. After hybridisation the slides were washed for 30 minutes in 50 ml preheated washing buffer (20 mM Tris-HCl, 0.9 M NaCl [pH 7.2]) and briefly rinsed in MilliQ. For staining all bacteria, the samples were incubated with 0.25 ng/l 4',6-diamidino-2-phenylindole (DAPI) in PBS for 5 minutes at room temperature. After DAPI staining the slides were briefly rinsed in MilliQ, dried, mounted with Vectashield (Vector Laboratories, Burlingame, Calif., U.S.A.) and covered with a coverslip. The slides were automatically analysed using an Olympus AX70 epifluorescence microscope with automated image analysis software (Analysis 3.2, Soft Imaging Systems GmbH, Münster, Germany). The percentage of bifidobacteria per sample was determined by analysing 25 randomly chosen microscopic positions. At each position the percentage of bifidobacteria was determined by counting all cells with a DAPI filter set (SP 100, Chroma Technology Corp., Brattleboro, U.S.A.) and counting all bifidobacteria using a Cy3 filter set (41007, Chroma Technology, Brattleboro, U.S.A.).

Short Chain Fatty Acids Analysis

The short chain fatty acids (SCFA) acetic, propionic, n-butyric, iso-butyric and n-valeric acids were quantitatively determined by a Varian 3800 gas chromatograph (GC) (Varian Inc., Walnut Creek, U.S.A.) equipped with a flame ionisation detector. 0.5 µl of the sample was injected at 80° C. in the column (Stabilwax, 15×0.53 mm, film thickness 1.00 µm, Restek Co., U.S.A.) using helium as a carrier gas (3.0 psi). After injection of the sample, the oven was heated to 160° C. at a speed of 16° C./min, followed by heating to 220° C. at a speed of 20° C./min and finally maintained at a temperature of 220° C. for 1.5 minutes. The temperature of the injector and detector was 200° C. 2-ethylbytyric acid was used as an internal standard.

Lactate Analysis

Homogenised faeces was thawed on ice and centrifuged for 5 minutes ant 14,000 rpm 100 µl supernatant was heated for 10 minutes at 100° C. to inactivate all enzymes. Lactate was determined enzymatically, using a L-lactate acid detection kit with D- and L-lactate-dehydrogenase (Boehringer Mannheim, Mannheim, Germany). Lactate was only determined in those faecal samples which were large enough.

pH Analysis

After storage at −20° C., faecal samples were thawed and the pH was directly measured in the faeces at room temperature using a Handylab pH meter (Scott Glas, Mainz, Germany) equipped with an Inlab 423 pH electrode (Mettler-Toledo, Columbo, U.S.A.)

Data Analysis

Prior to the study, power calculations showed that to detect a difference in percentage of bifidobacteria between the intervention formula group and the standard formula group of 30% with a SD of 25%, 13 infants per group should be included. Because of an expected drop out of 30% in the formula groups, more infants than calculated were included in the study. Statistical package SPSS (version 11/0) was used for statistical analysis of the results. All values were checked for normality by visual inspection of the normal probability plots. Differences in percentage bifidobacteria, pH, relative amounts of SCFA and lactate between the groups were tested for significance using analysis of variance. In case of a significant difference ($p<0.05$), groups were compared by using the Bonferroni post hoc test.

Because it is not possible to double blind assign breast and bottle-feeding and to ensure adequate randomisation, no statistical analysis were performed to compare the breast-feeding with any of the formula feeding groups. Data from the breast-fed group are only given when the infant was only fed breast milk at that time point.

2.2 Results

In total, 120 (-pro group infants were included. 57 infants started on formula feeding directly after birth and were equally divided among the formula groups. Of the 63 infants that were fed breast milk directly after birth, 24 switched to formula feeding before the age of 16 weeks and 5 infants dropped out. The characteristics of the study subjects are shown in Table 4. In the formula groups, 9 infants dropped out of the study within the first 16 weeks after birth (4 in the SF, 5 in the OSF group. Reasons for drop out included: colics, suspicion of cow's milk allergy, constipation and practical problems.

TABLE 4

Characteristics of study objects

|  |  | Standard Formula, SF N = 19 | Prebiotic formula, OSF N = 19 | Breast milk, BF N = 63 |
|---|---|---|---|---|
| Sex | Male | 5 | 12 | 33 |
|  | Female | 14 | 7 | 30 |
| Place of birth | At home | 7 | 8 | 40 |
|  | Hospital | 12 | 11 | 23 |
| Mode of delivery | Vaginal | 14 | 16 | 59 |
|  | Caesarean | 5 | 3 | 4 |
| Birth weight |  | 3600 ± 501 | 3318 ± 602 | 3651 ± 601 |

Faecal Bifidobacteria

The percentages of bifidobacteria in faeces at the age of 5 days, 10 days, 4, 8, 12, and 16 weeks of the feeding groups are shown in Table 5 and the amounts in Table 5. The OSF group tends to have a higher bifidobacteria % than the SF group from total bacterial count at all ages, but the differences were not statistically different. Unexpectedly, the percentage of Bifidobacteria in breast fed babies was also relatively low and were in line with the formula fed groups.

Preliminary data also show an increase in Lactobacilli in the BF and OSF group, but the amounts of Lactobacilli in the faecal flora are at least one order of magnitude lower than the Bifidobacteria, the overall pattern is changes very little.

pH Results

The pH values measured in the faeces of the formula-fed infants are shown in table 6. Lowest pH was found in infants fed on breast milk. Faecal pH of faeces of infants fed the OSF formula were lower than the SF group (p<0.045 at all ages except day 5).

SCFA Results

The total amount of SCFA in the faeces is shown in Table 5 below.

The percentage of the different SCFA from total SCFA are shown in Table 6. There are no statistically significant differences found in total SCFA concentration between the formula groups. Also the amount of SCFA is comparable to those of the other feeding groups. However, already after 10 days, differences in the SCFA profiles can be seen between infants fed on OSF or breast milk compared to infants fed on standard formula. Infants fed the formula containing GOS and polyfructose and fed breast milk, have higher percentages of acetate and lower percentages of propionate, butyrate, iC4-6 SCFA when compared to infants fed the standard formula.

Lactate Results

The concentrations lactate (mmol/kg faeces) of all groups are shown in Table 5. Already from 5 days of age, the OS formula (not sign.) and the groups of breast milk have higher amounts of lactate compared to the standard formula group. The relative amount of lactate (as a percentage of the sum of SCFA and lactate) is highest in breast fed babies and lowest in standard formula fed babies. Babies fed a formula containing TOS/inulin have an intermediate relative amount of acetate. The percentage of lactate in OSF fed babies at 16 weeks (relative to total acids) significantly differs from that of SF babies.

TABLE 5

Concentration of lactate and total SCFA (mmol/kg faeces) and Bifidobacteria (*1.10$^{13}$/kg faeces) pH between birth and 16 weeks of age. Mean ± SEM. Except for pH, no statistically differences were found.

|  |  | Lactate | SCFA | pH | Bifido-bacteria |
|---|---|---|---|---|---|
| 5 days | SF | 13.5 ± 7.7 | 54.7 ± 12.6 | 5.93 ± 0.15 | 0.58 ± 0.49 |
|  | OSF | 10.7 ± 4.3 | 56.5 ± 7.7 | 5.49 ± 0.15 | 1.20 ± 2.24 |
|  | BF | 13.3 ± 2.8 | 48.7 ± 4.4 | 5.27 ± 0.07 | 0.47 ± 0.39 |
| 10 days | SF | 4.6 ± 3.0 | 62.0 ± 7.9 | 6.88 ± 0.15 | 0.96 ± 0.83 |
|  | OSF | 9.7 ± 3.6 | 62.3 ± 7.2 | 5.95 ± 0.20 | 1.10 ± 0.99 |
|  | BF | 15.1 ± 3.2 | 54.7 ± 4.9 | 5.35 ± 0.07 | 0.48 ± 0.61 |
| 4 weeks | SF | 2.6 ± 1.4 | 68.3 ± 10.3 | 6.77 ± 0.21 | 0.97 ± 0.96 |
|  | OSF | 9.9 ± 3.4 | 83.1 ± 8.8 | 5.88 ± 0.18* | 1.20 ± 0.55 |
|  | BF | 22.8 ± 4.4 | 59.8 ± 4.8 | 5.45 ± 0.12 | 0.56 ± 0.64 |
| 8 weeks | SF | 7.6 ± 6.8 | 76.5 ± 13.2 | 6.80 ± 0.20 | 0.89 ± 0.56 |
|  | OSF | 24.4 ± 5.3 | 76.0 ± 8.4 | 5.68 ± 0.18* | 1.00 ± 0.52 |
|  | BF | 30.9 ± 5.3 | 62.8 ± 5.4 | 5.27 ± 0.15 | 0.58 ± 0.59 |
| 12 weeks | SF | 14.1 ± 9.4 | 73.9 ± 11.9 | 6.88 ± 0.20 | 0.91 ± 0.80 |
|  | OSF | 18.4 ± 7.0 | 76.1 ± 12.1 | 5.60 ± 0.18* | 1.30 ± 0.99 |
|  | BF | 42.1 ± 7.1 | 60.4 ± 4.9 | 5.29 ± 0.17 | 1.40 ± 1.38 |
| 16 weeks | SF | 1.7 ± 1.2 | 68.6 ± 14.0 | 7.09 ± 0.15 | 1.00 ± 0.80 |
|  | OSF | 18.5 ± 5.7 | 67.7 ± 11.7 | 5.60 ± 0.20* | 1.30 ± 0.76 |
|  | BF | 45.1 ± 9.0 | 59.2 ± 6.9 | 5.68 ± 0.24 | 0.89 ± 0.78 |

TABLE 6 relative amounts of SCFA (% of total SCFA), lactate (% of total acids), % Bifidobacteria between birth and 16 weeks of age.

| Day/week |  | Acetate | Propionate | Butyrate | Sum iC4-C5 | % Bifidobacteria | lactate |
|---|---|---|---|---|---|---|---|
| 5 d | SF | 84.3 ± 3.4 | 12.9 ± 3.2 | 1.7 ± 0.5 | 1.1 ± 0.4 | 45 ± 3.6 | 13.8 ± 18.5 |
|  | OSF | 85.8 ± 5.1 | 12.0 ± 4.7 | 0.5 ± 0.5 | 1.7 ± 0.7 | 50 ± 8.6 | 8.7 ± 13.3 |
|  | BF | 89.5 ± 1.8 | 7.0 ± 1.5 | 1.6 ± 0.4 | 2.0 ± 0.4 | 54 ± 4.1 | 12.5 ± 14.0 |
| 10 d | SF | 70.9 ± 2.0 | 21.3 ± 2.6 | 4.6 ± 1.1 | 3.2 ± 0.5 | 65 ± 6.0 | 4.3 ± 10.8 |
|  | OSF | 84 ± 2.4* | 13.5 ± 2.3 | 1.4 ± 0.4* | 1.1 ± 0.4 | 61 ± 6.3 | 8.2 ± 9.8 |
|  | BF | 89.3 ± 1.9 | 5.8 ± 1.3 | 2.3 ± 0.3 | 2.6 ± 0.4 | 42 ± 4.1 | 13.4 ± 13.8 |
| 4 w | SF | 71.8 ± 2.8 | 17.8 ± 3.3 | 5.0 ± 1.1 | 5.5 ± 2.6 | 52 ± 5.4 | 6.9 ± 16.4 |
|  | OSF | 77.7 ± 2.2 | 15.4 ± 2.0 | 5.8 ± 2.2 | 1.1 ± 0.3 | 71 ± 4.5 | 8.4 ± 10.7 |
|  | BF | 91.0 ± 1.8 | 4.3 ± 1.2 | 2.6 ± 0.6 | 2.1 ± 0.4 | 47 ± 5.4 | 19.6 ± 17.0 |

TABLE 6-continued relative amounts of SCFA (% of total SCFA), lactate (% of total acids), %
Bifidobacteria between birth and 16 weeks of age.

| Day/week | | Acetate | Propionate | Butyrate | Sum iC4-C5 | % Bifidobacteria | lactate |
|---|---|---|---|---|---|---|---|
| 8 w | SF | 74.6 ± 2.9 | 16.4 ± 2.0 | 6.1 ± 1.2 | 2.9 ± 0.7 | 50 ± 6.3 | 3.5 ± 9.9 |
|  | OSF | 83.5 ± 2.7 | 11.4 ± 2.1 | 3.7 ± 1.2 | 1.4 ± 0.4 | 64 ± 4.1 | 17.7 ± 15.2 |
|  | BF | 91.2 ± 1.6 | 5.4 ± 1.4 | 1.9 ± 0.5 | 1.6 ± 0.3 | 41 ± 4.5 | 21.7 ± 13.4 |
| 12 w | SF | 73.9 ± 2.9 | 17.8 ± 3.3 | 5.0 ± 1.1 | 3.2 ± 0.5 | 56 ± 5.4 | 5.4 ± 11.9 |
|  | OSF | 86.5 ± 2.1 | 11.2 ± 1.8 | 1.2 ± 0.3* | 1.0 ± 0.4 | 60 ± 5.0 | 13.6 ± 13.2 |
|  | BF | 86.1 ± 3.3 | 7.5 ± 2.2 | 3.0 ± 0.7 | 3.5 ± 0.8 | 59 ± 4.5 | 30.2 ± 16.3 |
| 16 w | SF | 69.9 ± 3.9 | 19.6 ± 2.7 | 5.6 ± 0.9 | 4.9 ± 0.8 | 52 ± 6.3 | 0.6 ± 0.9 |
|  | OSF | 82.2 ± 5.3 | 14.3 ± 4.9 | 2.1 ± 0.5* | 1.5 ± 0.4* | 69 ± 7.7 | 16.4 ± 12.0* |
|  | BF | 89.7 ± 2.7 | 6.4 ± 2.1 | 1.6 ± 0.4 | 2.2 ± 0.5 | 47 ± 6.3 | 35.6 ± 20.4 |

$P < 0.05$ compared to SF;
SF = standard formula fed,
OSF = SF supplemented with GOS + inulin;
BF = breast fed.

The above demonstrates that in faeces of infants fed with this combination of GOS and polyfructose the pH is lowered, that more lactate is formed, and that an acid (acetate and lactate) pattern is formed which is more similar to that of breast fed babies and that this effect cannot be attributed to the quantitative increase of Bifidobacteria.

Example 3—Beneficial Effects of Lactate and SCFA Mixture on Muc-2, PGE1 and PGE2 Expression 3.1 Material and Methods The effect of lactate and a SCFA mixture was analysed as described in Willemsen, L E M, Koetsier M A, van Deventer S J H, van Tol E A F (2003), Gut 52:1442-1447, with the following modifications: Lactate and a mixture of acetate/propionate/butyrate 90/5/5 was tested. For the mucus production experiments a co-culture of CCD18 and T84 cells was used, whereas for the PGE1 and PGE2 production experiments a monoculture of CCD18 cells was used.

3.2 Results

SCFA, in a mixture of 90/5/5 (acetate/propionate/butyrate), and L-lactate dose dependently induces MUC-2 expression in a co-culture of CCD18 and T84 cells as can be seen in FIG. 4A. Also the concentration of PGE1 and PGE2 increases in CCD18 cells as can be seen in FIG. 4B. At higher concentrations of the added organic acids the increases reaches statistically significance.

Example 4: Effect of Lactate on Colon Contraction 4.1 Material and Methods

Male Wistar rats (CKP/Harlan, Wageningen/Horst, Netherlands) were housed under conditions of controlled temperature and light cycle and were provided free access to food pellets and water. Animals were anaesthetised by a mixture of $N_2O$, $O_2$ and isofluran, the abdomen was opened and the colon was removed immediately. The tissue was placed in Krebs-Henseleit buffer pH 7.4 (composition in mM: 118.0 NaCl, 4.75 KCl, 1.18 $MgSO_4$, 2.5 $CaCl_2$, 10 glucose, 1.17 $KH_2PO_4$ and 24.9 $NaHCO_3$).

The colon was cut into a distal and a proximal portion and was rinsed with Krebs-Henseleit buffer while gently squeezing out faecal content. To approximate in vivo conditions as closely as possible, 1 cm fully intact segments were attached longitudinally to an isometric force transducer (F30 type 372, HSE, Germany) in 20 ml water-jacketed (37° C.) organ baths (Schuler, HSE, Germany) containing Krebs-Henseleit buffer gassed continuously with 95% $O_2$-5% $CO_2$. The segments were gradually stretched to a resting tension of 1 g and allowed to equilibrate for 45 minutes with intermittent washings. The tensions of the segments in rest and in response to different stimuli were amplified by a transducer amplifier module (HSE, Germany) and recorded on a multipen recorder (Rikadenki, HSE, Germany).

The segments were incubated with 40 mM KCl for 5 minutes and the contractile responses were measured. KCl was washed out by three consecutive washes at 5 minutes intervals. The segments were then incubated with increasing concentrations up to 100 mM of acetate or sodium-L-lactate. The acid solutions were prepared freshly in distilled water. NaOH was added to acetate to obtain a neutral pH. At the end of the incubation with a fatty acid, 40 mM KCl was added to determine whether the contractile response to KCl was influenced by the fatty acid. Before a new incubation the segments were allowed to equilibrate for 45 minutes in fresh Krebs-Henseleit buffer with intermittent washings.

The experimental protocol consisted of two proximal and two distal sections of the colon. For data analysis (n=3), the contraction level induced by the stimuli was defined as the tension in g after 5 minutes incubation. Data obtained from identical segments (proximal or distal) were used to calculate a mean value and each segment served as its own control sample.

4.2 Results

Figure 5:
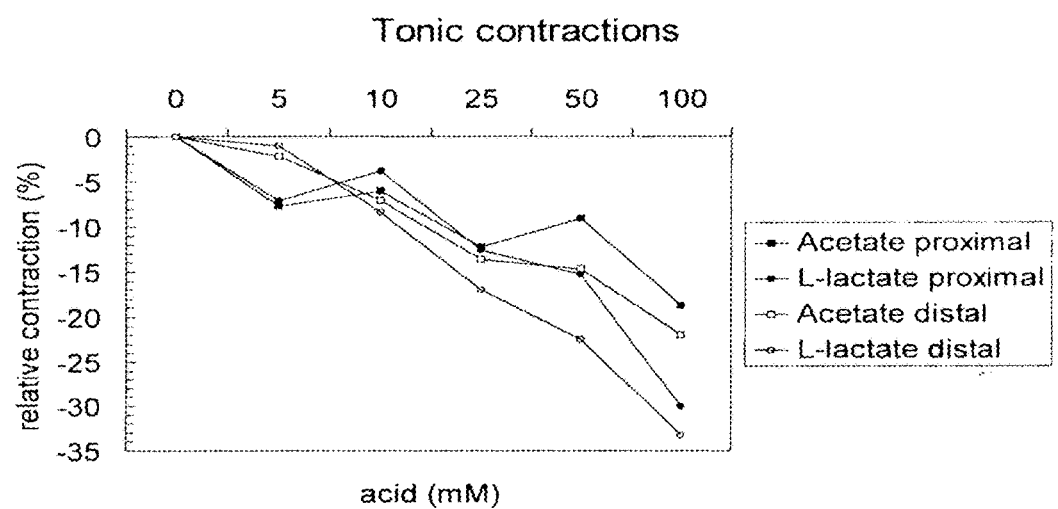

As can be seen from FIG. 5, sodium acetate and especially sodium-L-lactate decrease the tension of tonic contractions. The relaxation effects are higher in the distal part of the colon than in the proximal part of the colon.

Also the number of spontaneous contractions, the phasic contractions, decrease in the proximal part of the colon upon addition of the sodium acetate and sodium-L-lactate, whereas no effects are observed in the distal part of the colon.

In the proximal part of the colon the tonic contractions as a response to KCl, however, are comparable in the presence or absence of 25 mM sodium acetate or sodium L-lactate. At higher concentrations a significant relaxation is observed even after addition of KCl.

The invention claimed is:

1. A method of treating eczema, the method consisting of orally administering to a mammal suffering from eczema a composition comprising galactooligosaccharide and polyfructose, wherein the weight ratio of galactooligosaccharide:polyfructose is 97:3 to 80:20, wherein the composition does not comprise lactobacilli.

2. The method according to claim 1, wherein the weight ratio of galactooligosaccharide:polyfructose is 95:5 to 85:15.

3. The method according to claim 1, wherein the weight ratio of galactooligosaccharide:polyfructose is about 90:10.

4. The method according to claim 1, wherein the galactooligosaccharide is transgalacto-oligosaccharide.

5. The method according to claim 1, wherein the polyfructose is inulin.

6. The method according to claim 1, wherein the galactooligosaccharide is transgalacto-oligosaccharide and the polyfructose is inulin.

7. The method according to claim 5, wherein the inulin has an average degree of polymerization of 20 to 150.

8. The method according to claim 6, wherein the inulin has an average degree of polymerization of 20 to 150.

9. The method according to claim 1, wherein the composition is liquid.

10. The method according to claim 1, wherein the mammal is a human child, teenager or adult.

11. The method according to claim 1, wherein the mammal is a human infant.

12. The method according to claim 11, wherein the human infant is up to a 12 months old infant.

13. The method according to claim 1, wherein the composition does not comprise lactobacilli and bifidobacteria.

* * * * *